(12) United States Patent
Lee et al.

(10) Patent No.: US 10,858,661 B2
(45) Date of Patent: Dec. 8, 2020

(54) **USE OF *METHYLOMONAS* SP. DH-1 STRAIN AND ITS TRANSFORMANTS**

(71) Applicant: University-Industry Cooperation Group of Kyung Hee University, Gyeonggi-do (KR)

(72) Inventors: Eun Yeol Lee, Seoul (KR); In Yeub Hwang, Gyeonggi-do (KR); So Hyeon Oh, Gyeonggi-do (KR); Ok Kyung Lee, Gyeonggi-do (KR); Young Chan Jeon, Incheon (KR); Thi Ngoc Diep Nguyen, Gyeonggi-do (KR); Duc Anh Nguyen, Gyeonggi-do (KR); Hye Jin Kim, Gyeonggi-do (KR); Thi Thu Nguyen, Gyeonggi-do (KR)

(73) Assignee: University-Industry Cooperation Group of Kyung Hee University, Gyeonggi-do (KR)

(*) Notice: Subject to any disclaimer, the term of this patent is extended or adjusted under 35 U.S.C. 154(b) by 0 days.

(21) Appl. No.: 16/477,158

(22) PCT Filed: Jan. 10, 2018

(86) PCT No.: PCT/KR2018/000500
§ 371 (c)(1),
(2) Date: Jul. 10, 2019

(87) PCT Pub. No.: WO2018/131898
PCT Pub. Date: Jul. 19, 2018

(65) Prior Publication Data
US 2020/0123552 A1    Apr. 23, 2020

(30) Foreign Application Priority Data

| Jan. 10, 2017 | (KR) | 10-2017-0003301 |
| Jan. 10, 2017 | (KR) | 10-2017-0003302 |
| Mar. 31, 2017 | (KR) | 10-2017-0041834 |
| May 10, 2017 | (KR) | 10-2017-0057991 |
| Sep. 13, 2017 | (KR) | 10-2017-0117324 |

(51) Int. Cl.
| C12N 15/74 | (2006.01) |
| C12N 9/04 | (2006.01) |
| C12N 9/10 | (2006.01) |
| C12P 5/02 | (2006.01) |
| C12P 7/06 | (2006.01) |
| C12P 7/18 | (2006.01) |
| C12P 7/46 | (2006.01) |
| C12P 13/04 | (2006.01) |

(52) U.S. Cl.
CPC ........... *C12N 15/74* (2013.01); *C12N 9/0006* (2013.01); *C12N 9/1029* (2013.01); *C12P 5/026* (2013.01); *C12P 7/065* (2013.01); *C12P 7/18* (2013.01); *C12P 7/46* (2013.01); *C12P 13/04* (2013.01); *C12Y 101/01041* (2013.01); *C12Y 101/01042* (2013.01); *C12Y 203/01037* (2013.01)

(58) Field of Classification Search
CPC .... C12Y 101/01042; C12Y 101/01041; C12Y 203/01037; C12N 15/74; C12N 15/63; C12N 9/10; C12N 9/1029; C12N 9/88; C12N 9/0006; C12P 7/18; C12P 5/026; C12P 7/065; C12P 7/46; C12P 5/02; C12P 13/04
See application file for complete search history.

(56) References Cited

U.S. PATENT DOCUMENTS

| 9,399,783 | B2 | 7/2016 | Coleman et al. | |
| 9,551,013 | B2* | 1/2017 | Razavi-Shirazi | C12M 23/34 |
| 2006/0046288 | A1 | 3/2006 | Ka-Yiu et al. | |
| 2008/0293101 | A1 | 11/2008 | Peters et al. | |
| 2015/0315599 | A1* | 11/2015 | Shetty | C12P 7/40 435/6.18 |

FOREIGN PATENT DOCUMENTS

| JP | 2009535062 A | 10/2009 | |
| JP | 2015-149978 | 8/2015 | |
| KR | 1020030034166 A | 5/2003 | |
| KR | 10-2011-0071128 | 6/2011 | |
| KR | 10-2014-0092950 | 7/2014 | |
| KR | 20150069976 A | 6/2015 | |
| KR | 20150121789 A | 10/2015 | |
| KR | 20160105611 A | 9/2016 | |
| KR | 10-2017-0026084 | * 3/2017 | ............... C12N 1/20 |
| KR | 10-2017-0087361 | 7/2017 | |
| KR | 20170086931 A | 7/2017 | |
| KR | 10-2017-0089227 | 8/2017 | |
| WO | WO-2012124890 A2 | 9/2012 | |
| WO | WO-2015/155791 A2 | 10/2015 | |
| WO | WO 2016/165025 A1 | * 10/2016 | ............... C12N 1/21 |

OTHER PUBLICATIONS

Englund et al., Production of squalene in *Synechocystis* sp. PCC6803. PLOS One, 2014, vol. 9(3):, e90270: 1-9. (Year: 2014).*
Hur et al., Highly efficient bioconversion of methane to methanol using a novel type I *Metylomonas* sp. DH-1 newly isolated from brewery waste sludge. J Chem Technol Biotechnol., 2017, vol. 92: 311-318. (Year: 2017).*

(Continued)

*Primary Examiner* — Ganapathirama Raghu
(74) *Attorney, Agent, or Firm* — Cesari and McKenna, LLP

(57) ABSTRACT

The present invention relates to a method for producing various metabolites from a gas-phase alkane compound using a *Methylomonas* sp. DH-1 strain, deposited under Accession Number KCTC18400P, or a transformant thereof. The method provided in the present invention enables more effective production of various metabolites from a gaseous alkane compound compared to the conventional method using methanotrophic bacteria, and thus, the method of the present invention can be widely used for production of a target material using a bioreactor.

19 Claims, 10 Drawing Sheets
Specification includes a Sequence Listing.

(56) References Cited

OTHER PUBLICATIONS

Hur et al., Selective bio-oxidation of propane to acetone using methane-oxidizing *Metylomonas* sp. DH-1. J Ind Microbiol Biotechnol., 2017, vol. 44: 1097-1105. (Year: 2017).*

Suwanto A., Genetically engineered Rhodobacter sphaeroides for the overproduction of d-aminolevulinic acid. Appl Microbiol Biotechnol., 1999, vol. 51: 794-799. (Year: 1999).*

Ng et al.; "Production of 2,3-butanediol in *Saccharomyces cerevisiae* by in silico aided metabolic engineering"; Microbial Cell Factories, 2012, pp. 1-14, vol. 11:68.

Gao et al.; "An Artificial Enzymatic Reaction Cascade for a Cell-free Bio-system Based on Glycerol" Green Chem., 2014, DOI: 10.1039/C4GC01685H.

Zhang et al.; "Biotechnological production of acetoin, a 1 bio-based platform chemical, from lignocellulosic resource by metabolically engineered *Enterobacter cloacae*"; Green Chem., 2015, DOI: 10.1039/C5GC01638J.

Hwang et al.; "P0445 Redirecting one-carbon assimilation pathway"; Department of Chemical Engineering, Kyung Hee University, Gyeonggi-do, Republic of Korea; Oct. 2016, p. 355.

Notice of Allowance dated Sep. 23, 2019 in Corresponding Korean Patent Application No. 1020170003301.

Hur et al; "Highly efficient bioconversion of methane to methanol using a novel type I *Methylomonas* sp. DH-1 newly isolated from brewery waste sludge"; Society of Chemical Industry; J Chem Technol Biotechnol; 2017; 92: 311-318.

Nguyen et al, "Transcriptomic analysis of C1 and secondary metabolite pathways in a novel type I *Methylomonas* sp. DH1 possessing both RuMP and serine pathways cultured on methane and methanol" The Korean Society for Biotechnology and Bioengineering; Oct. 2016, p. 369.

GenBank Accession No. WP_004175750 "Multispecies: acetolactate synthase [Enterobacteriaceae]" Jul. 21, 2015.

GenBank Accession No. WP_002908205 "Multispecies: alpha-acetolactate decarboxylase [Enterobacteriaceae]" Jul. 21, 2015.

GenBank Accession No. WP_004151179 "Multispecies: diacetyl reductase ((S)-acetoin forming) [Enterobacteriacae]" Nov. 7, 2015.

Hur et al; "*Methylomonas* sp. DH-1, complete genome"; NCBI GenBank: CP014360.1; May 16, 2016.

Zhu et al; "Engineering of Acetate Recycling and Citrate Synthase to Improve Aerobic Succinate Production in Corynebacterium glutamicum" Plos One; Apr. 2013; vol. 8, Issue 4; e60659.

Wendisch et al., "Regulation of acetate metabolism in Corynebacterium glutamicum: transcriptional control of the isocitrate lyase and malate synthase genes" Archives of Microbiology (1997) 168:262-269.

Hwang et al. "Biocatalytic Conversion of Methane to Methanol as a Key Step for Development of Methane-Based Biorefineries"; J. Microbiol. Biotechnol.; Dec. 2014, pp. 1598-1605, vol. 24, No. 12.

Notice of Allowance dated Jul. 19, 2019 in Corresponding Korean Patent Application No. 1020170003302.

* cited by examiner

[FIG. 1A]
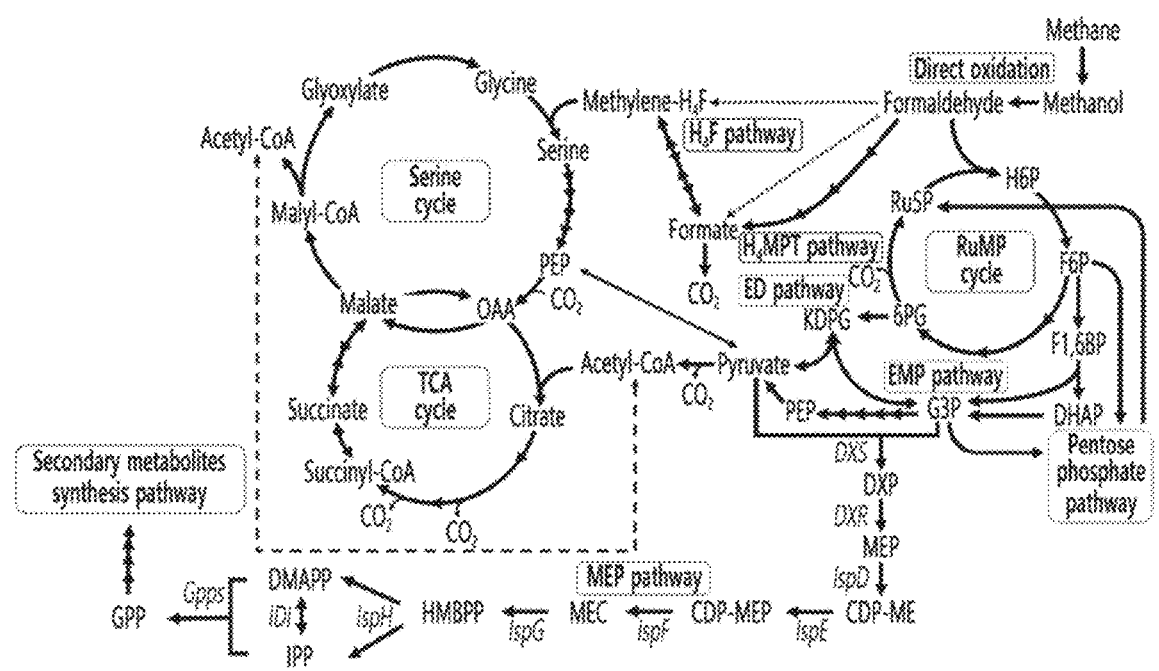

[FIG. 1B]
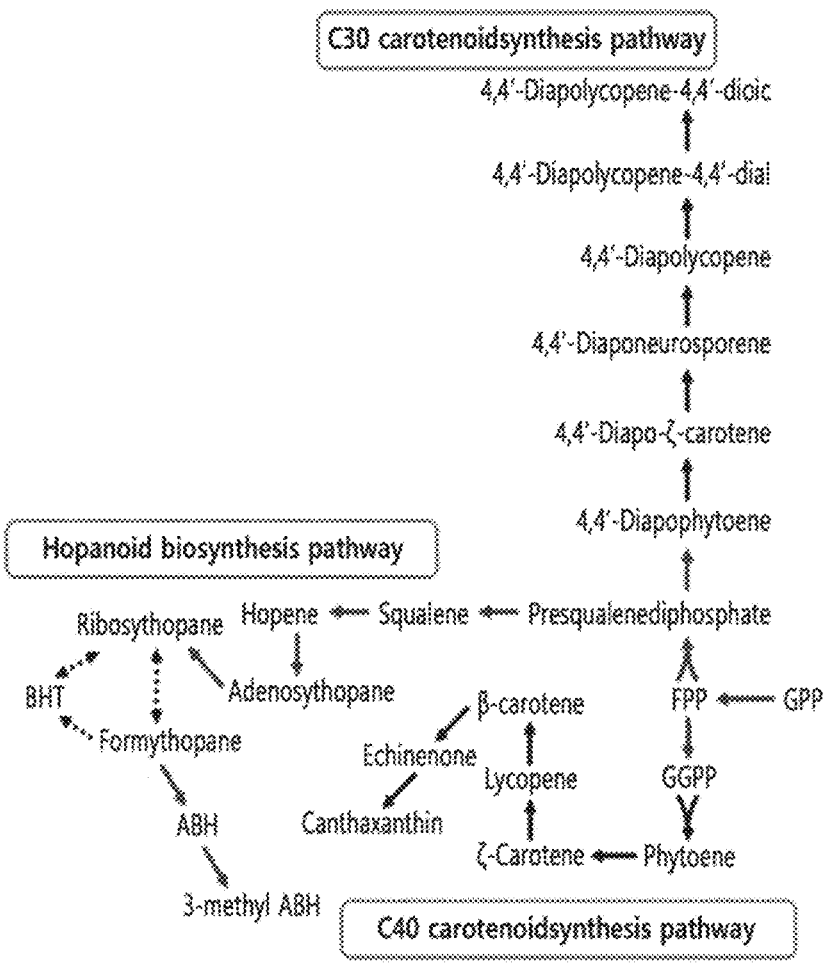

[FIG. 2A]
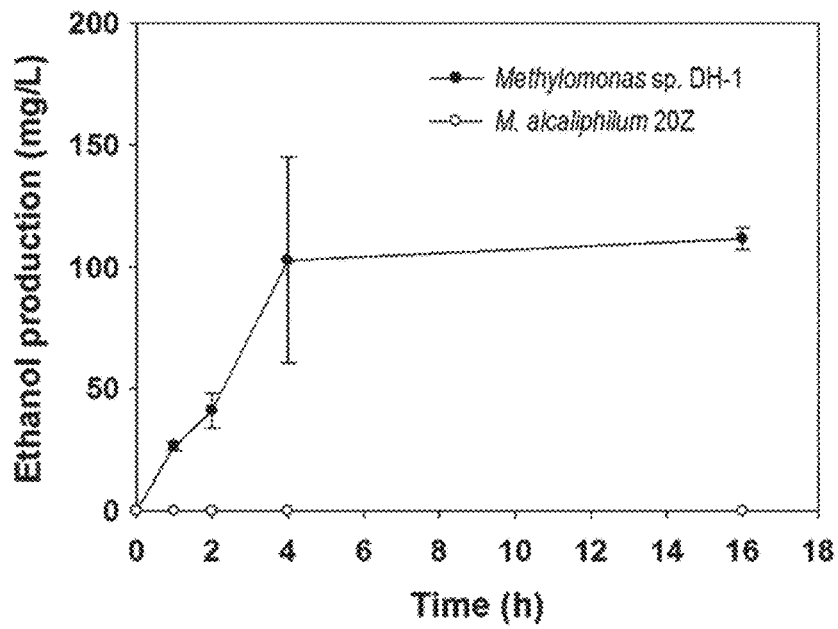
[FIG. 2B]
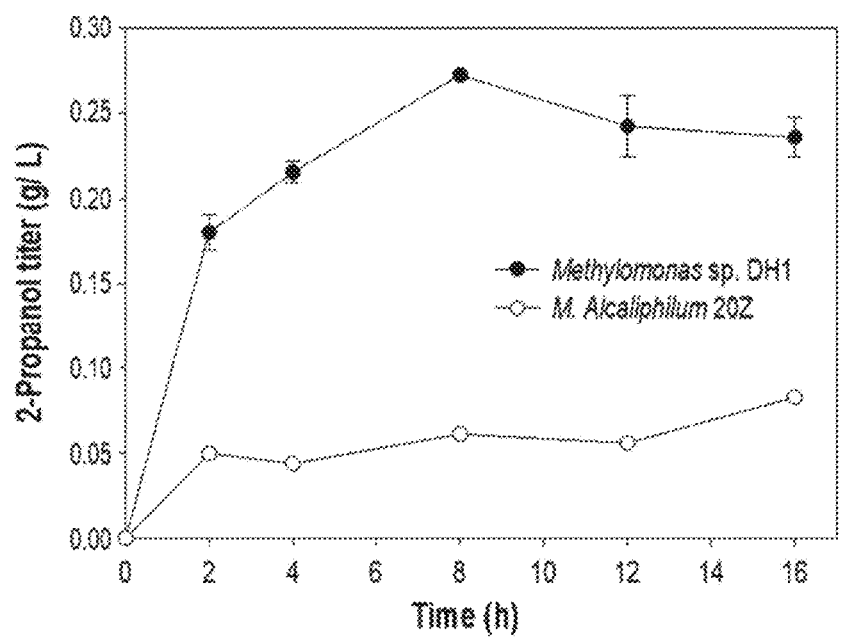

[FIG. 3A]
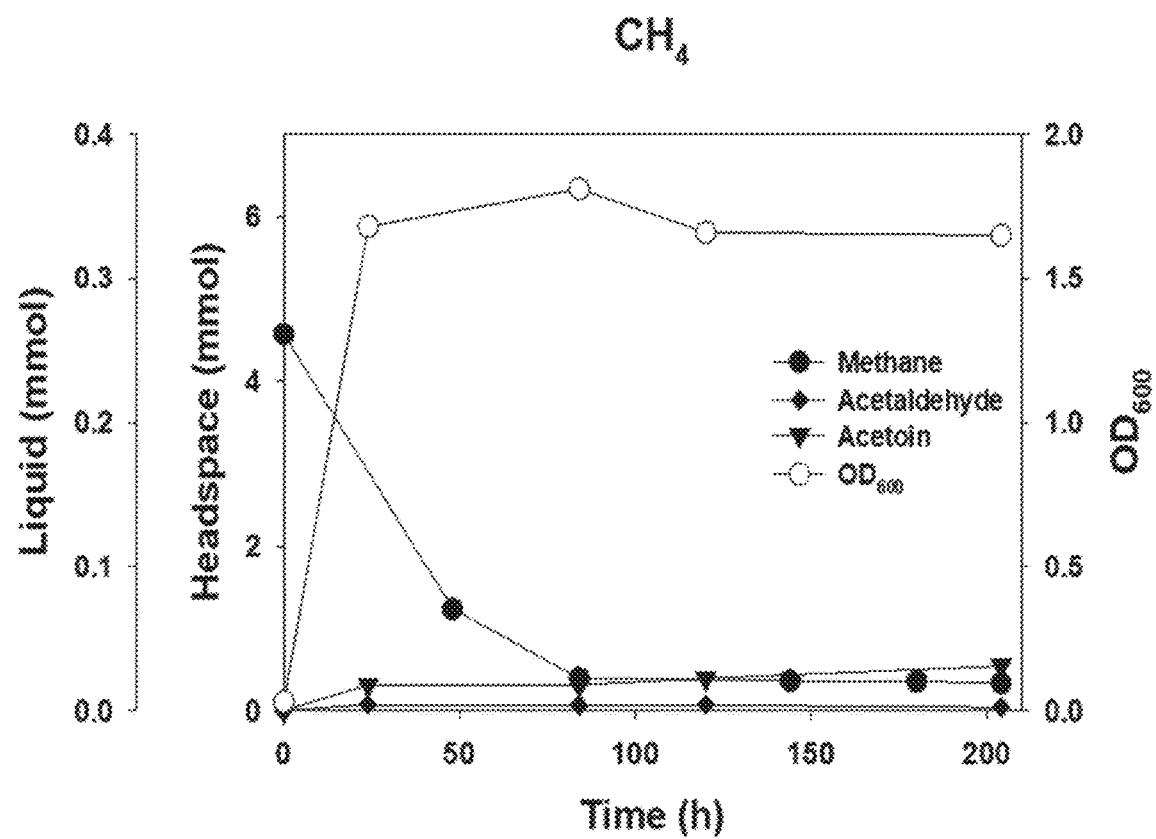

[FIG. 3B]
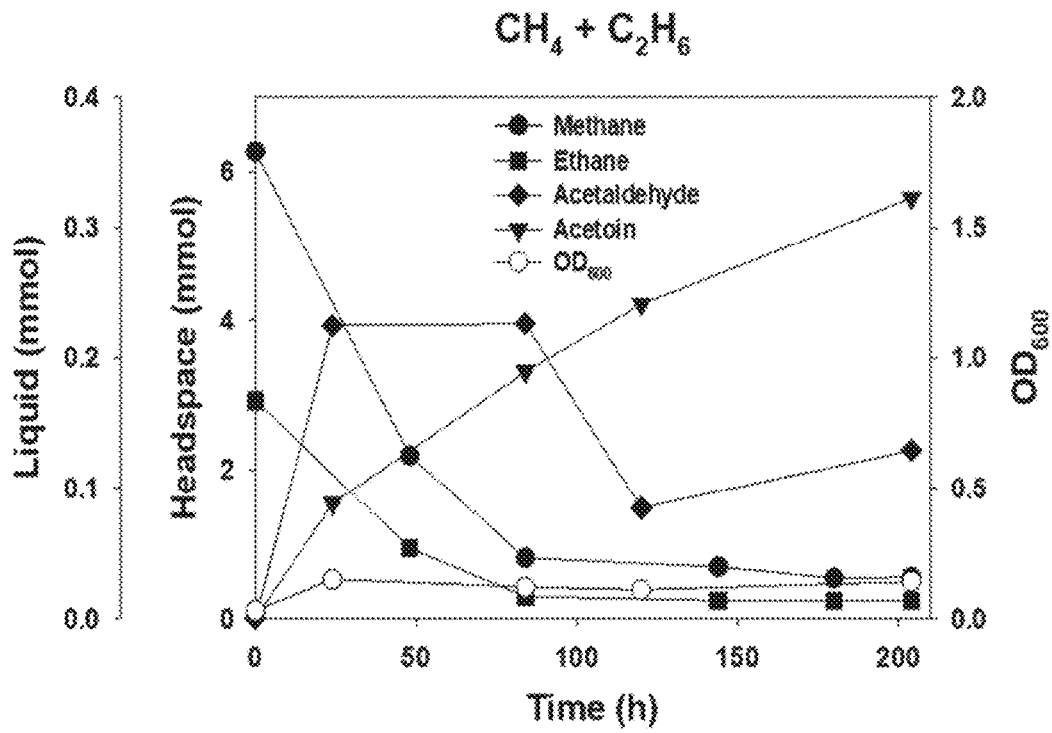
[FIG. 3C]
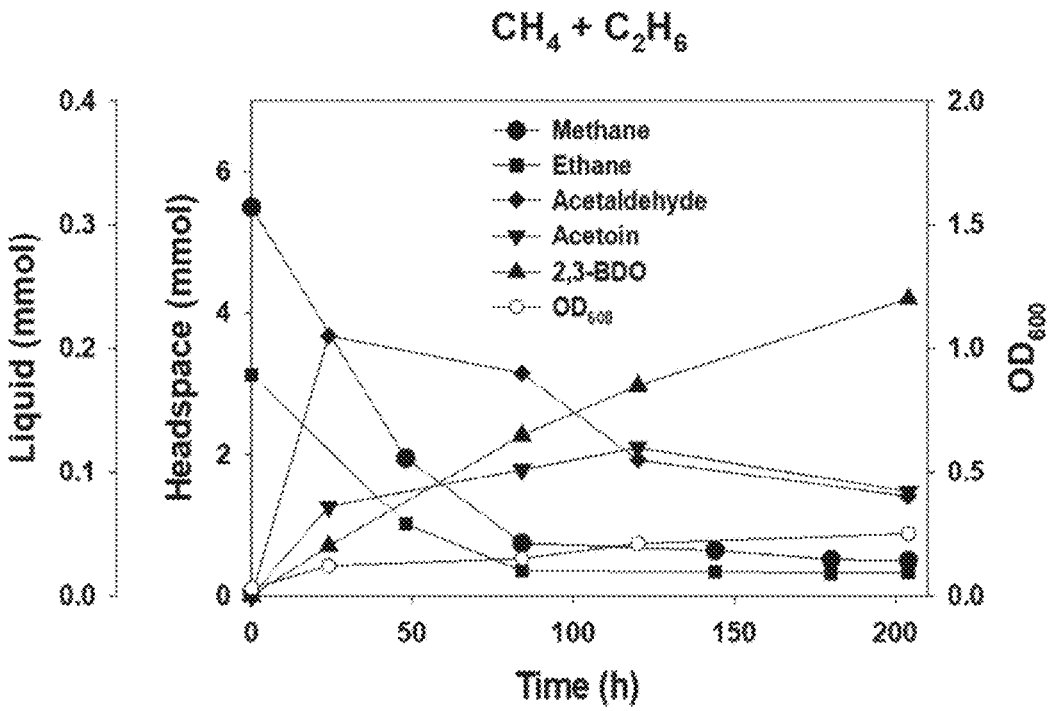

[FIG. 4A]
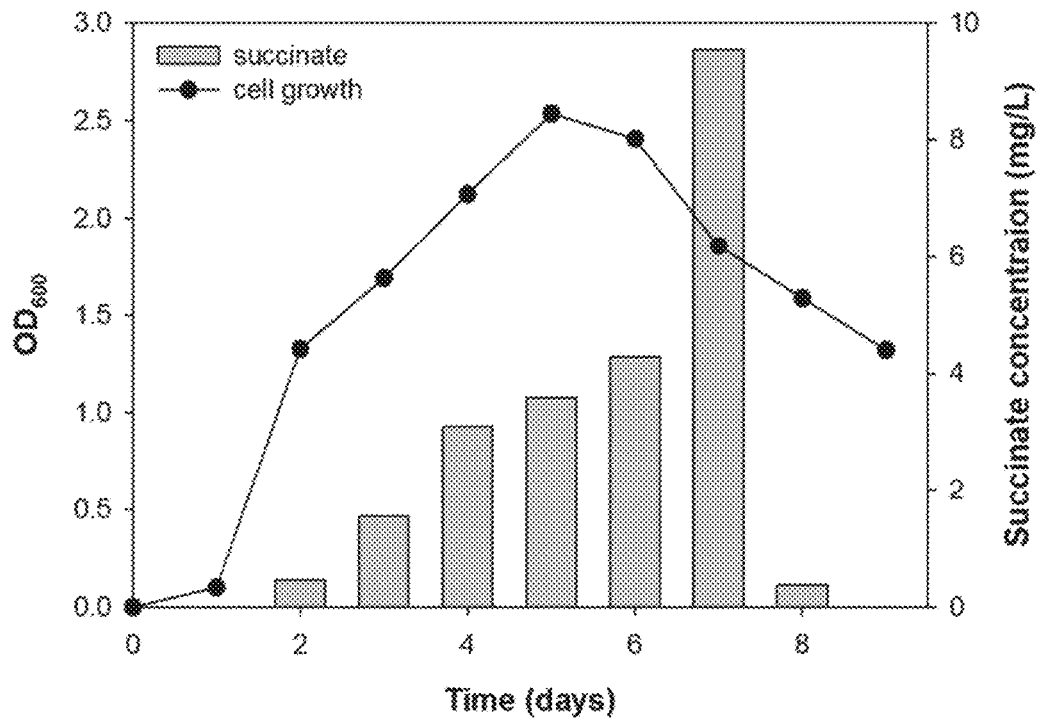
[FIG. 4B]
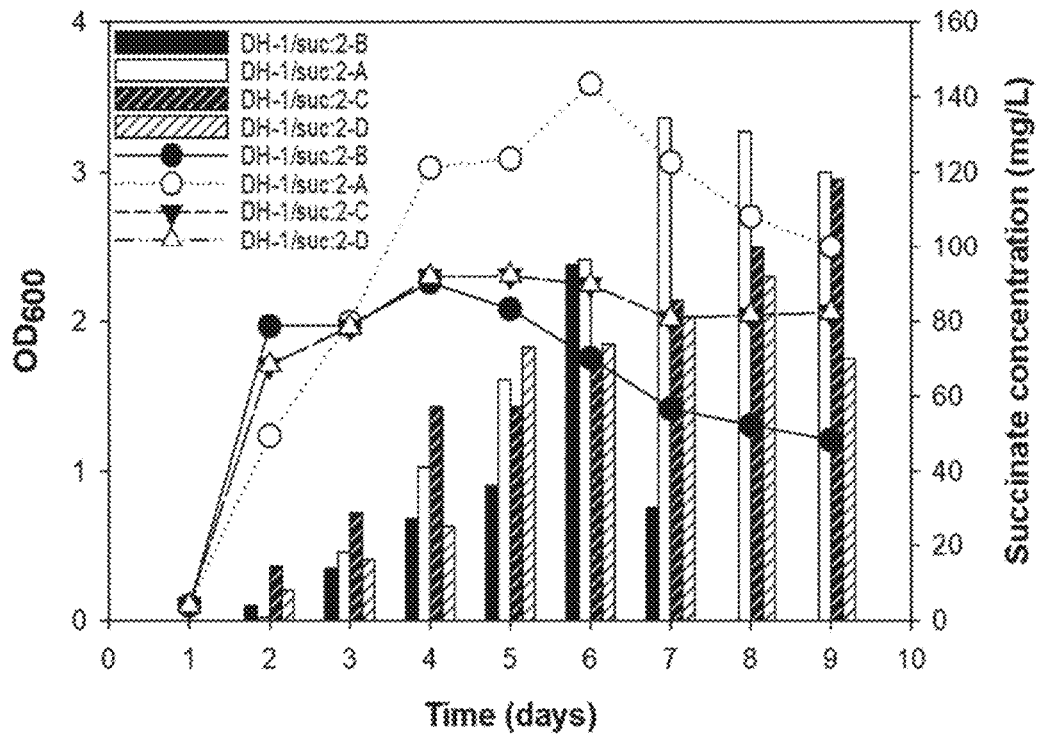

[FIG. 5]
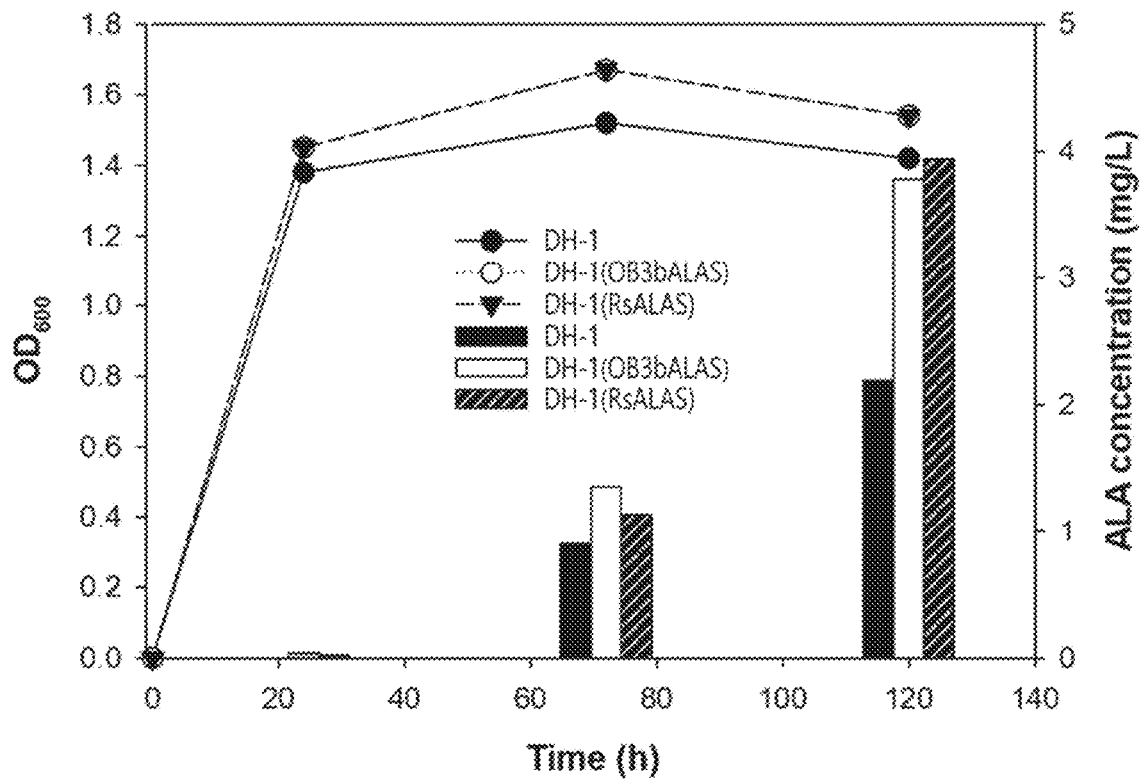
[FIG. 6]
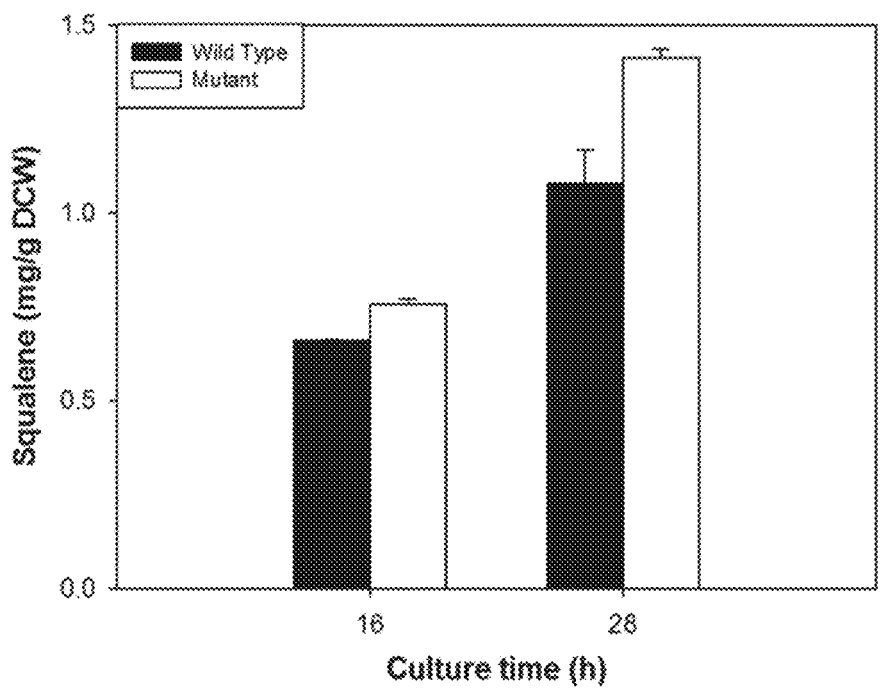

[FIG. 7A]
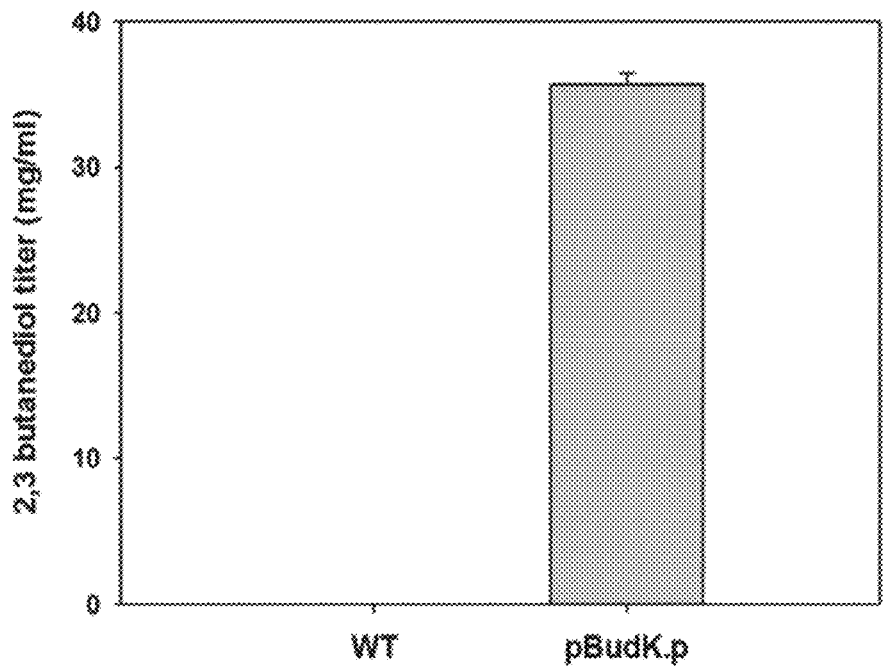
[FIG. 7B]
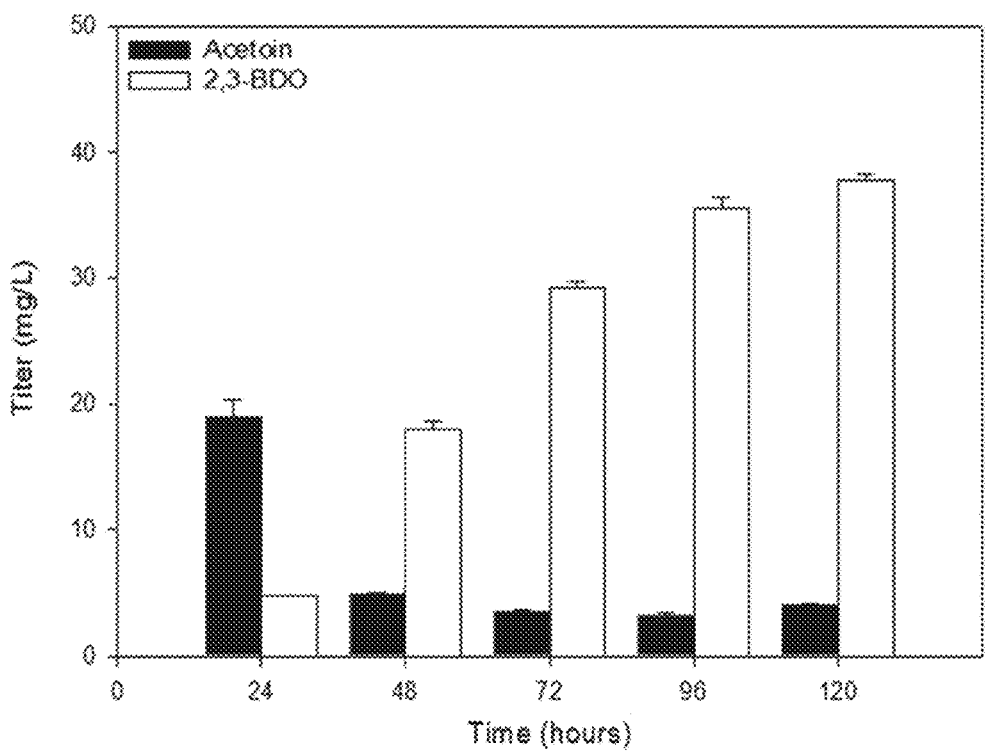

[FIG. 7C]
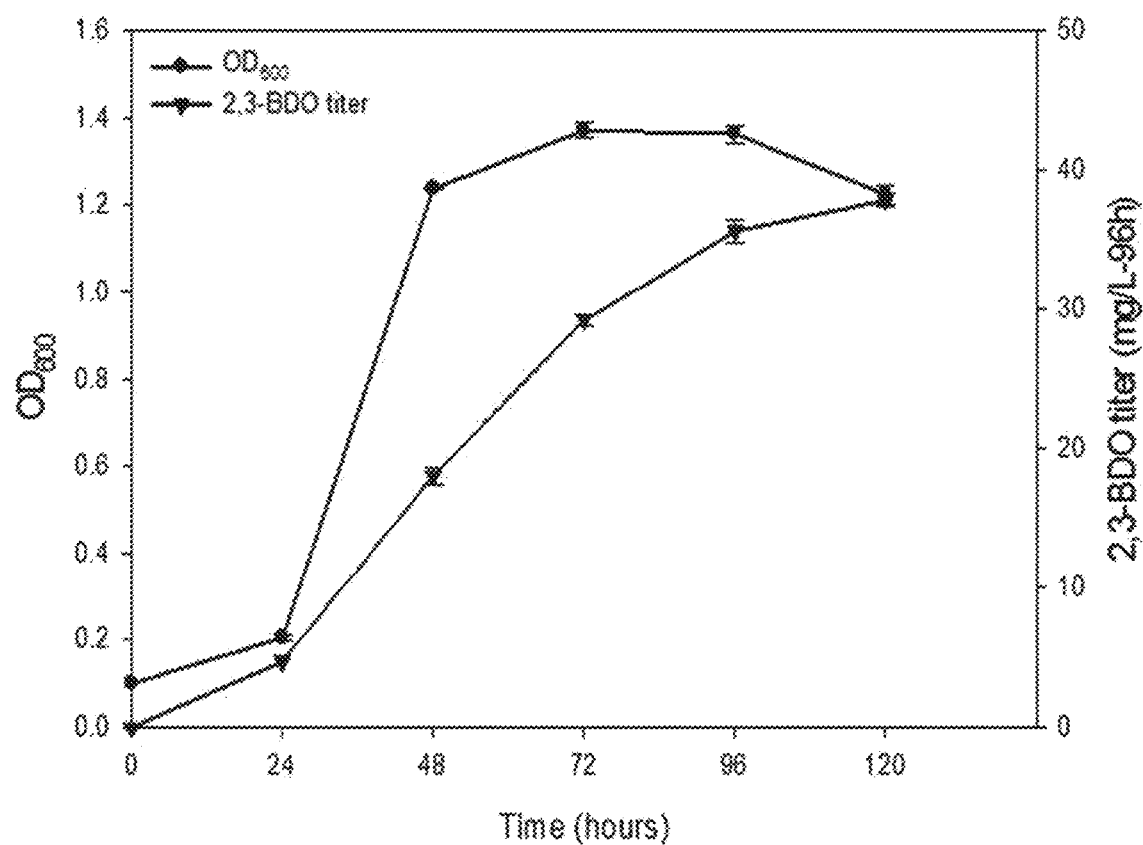

[FIG. 8A]
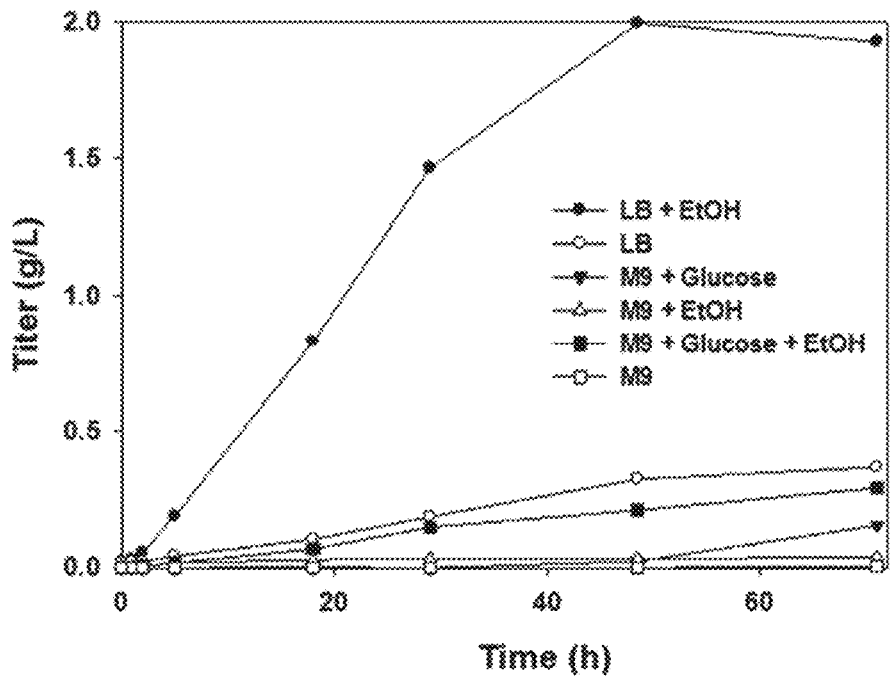
[FIG. 8B]
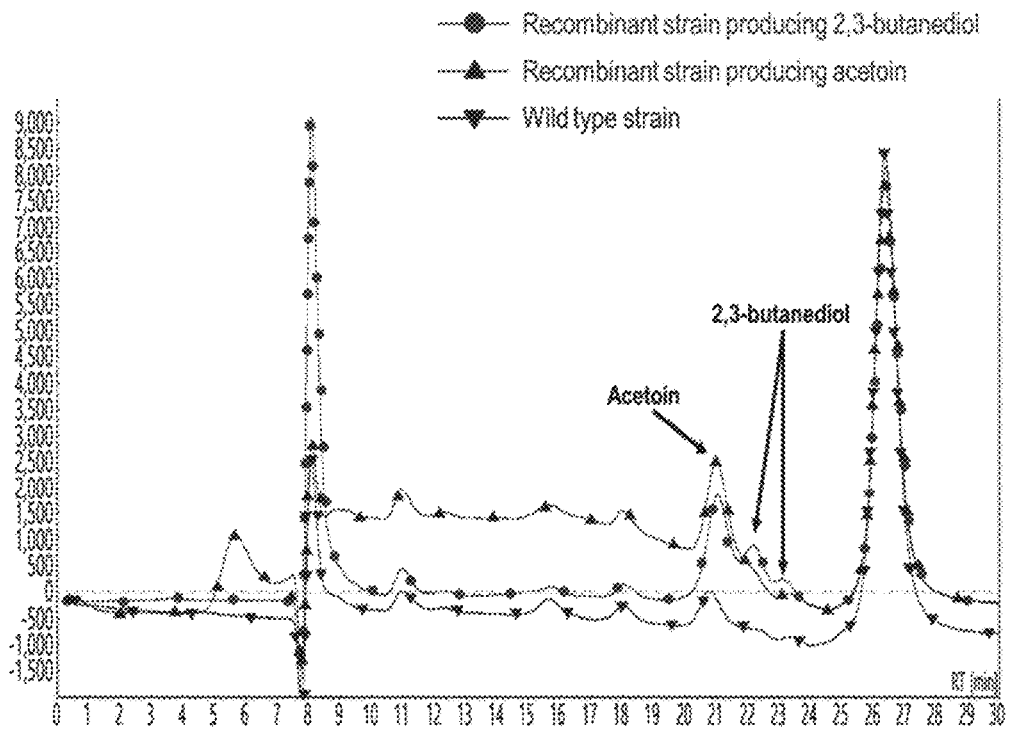

USE OF *METHYLOMONAS* SP. DH-1 STRAIN AND ITS TRANSFORMANTS

CROSS-REFERENCE TO RELATED APPLICATIONS

This application is the National Stage of International Application No. PCT/KR2018/000500, filed Jan. 10, 2018, which claims the benefit of Korean Application Nos. 10-2017-0003301, filed on Jan. 10, 2017, 10-2017-0003302, filed on Jan. 10, 2017, 10-2017-0041834, filed on Mar. 31, 2017, 10-2017-0057991, filed on May 10, 2017, and 10-2017-0117324, filed on Sep. 13, 2017. The contents of each application are hereby incorporated by reference in their entirety.

TECHNICAL FIELD

The present invention relates to a novel use of a *Methylomonas* sp. DH-1 strain, and more specifically, to a method for producing various metabolites from a gas-phase alkane compound using a *Methylomonas* sp. DH-1 strain deposited under Accession Number KCTC18400P, or a transformant thereof.

BACKGROUND ART

Global warming has increasingly drawn attention and concern across the world, and the main cause is known to be the greenhouse effect of carbon dioxide, methane, etc. To solve this problem, research has been actively carried out to discover a method for producing high value-added products from carbon dioxide using microorganisms which utilize carbon dioxide. In this regard, a recent study focused on the reconstruction of the metabolic pathway using a synthetic biocatalyst which was designed and computed using a computer to convert carbon dioxide.

The main sources of methane are biogas (a product of anaerobic digestion) and natural gas (a product of nature). Biogas mainly consists of methane and carbon dioxide. Methane accounts for 70% to 90% of natural gas, and the remainder consists of ethane and propane (in trace amounts). Recently, the production of shale gas (natural gas produced in the shale layer) has increased rapidly, and the use of methane and ethane is of high interest. As a result, studies on methanotrophs (i.e., microorganisms capable of utilizing methane) are actively underway.

Methanotrophs are prokaryotes which are able to utilize single-carbon substrates, including methane, as their only carbon source and energy source. Since methanotrophs possess methane monooxygenase, they can oxidize methane into methanol and then convert it to biomass after a series of metabolic processes. Methane monooxygenase is classified into soluble methane monooxygenase (sMMO) and particulate methane monooxygenase (pMMO). pMMO has a higher affinity for methane than sMMO and is thus considered to be a major biocatalyst in cells that grow by oxidizing methane, and enables conversion of methanol at room temperature and atmospheric pressure via hydrogenation of methane at room temperature and atmospheric pressure.

In an environment where copper is present, the expression of pMMO is induced while the expression of sMMO is suppressed simultaneously. pMMO is a membrane protein present in the cell membrane and serves to oxidize methane. Methanol, which is produced by oxidation of methane, is a high value-added product that can be variously used as a chemical and a biofuel. Therefore, studies on methane-methanol conversion using methanotrophs are underway both domestically and abroad.

Meanwhile, the methanotrophs may convert methane to various metabolites through various metabolic processes. For example, KR Patent Application Publication No. 2017-0087361 discloses a method for producing acetone using methanotrophs, and KR Patent Application Publication No. 2017-0089227 discloses a method for producing isoprene using halophilic methanotrophs.

However, these methods generally involve introducing a foreign gene into a methanotroph, or preparing a transformant in which the expression of an endogenous gene of the methanotroph is suppressed, and then producing various metabolites using the prepared transformant as a bioreactor. These methods have a disadvantage in that the production efficiency of the desired metabolites changes depending on the type of methanotrophs.

DISCLOSURE

Technical Problem

The present inventors have made efforts to develop a method for more effectively producing metabolites, and as a result, they have found that various metabolites can be more effectively produced from a gaseous alkane compound when a *Methylomonas* sp. DH-1 strain, deposited under Accession Number KCTC18400P, or a transformant thereof is used, thereby completing the present invention.

Technical Solution

An object of the present invention is to provide a method for producing various metabolites from a gaseous alkane compound using a *Methylomonas* sp. DH-1 strain, deposited under Accession Number KCTC18400P, or a transformant thereof.

Advantageous Effects of the Invention

It is possible to more effectively produce various metabolites from a gaseous alkane compound using the method provided in the present invention compared to when conventional methanotrophs were used, and thus the method of the present invention can be widely used for producing desired materials using a bioreactor.

BRIEF DESCRIPTION OF DRAWINGS

FIG. 1A is a schematic diagram showing various metabolic pathways activated in the DH-1 strain of the present invention.

FIG. 1B is a schematic diagram showing a metabolic pathway for synthesizing secondary metabolites activated in the DH-1 strain of the present invention.

FIG. 2A is a graph showing the comparison results of the concentrations of ethanol produced by the control strain and the DH-1 strain of the present invention.

FIG. 2B is a graph showing the comparison results of the concentrations of propanol produced by the control strain and the DH-1 strain of the present invention.

FIG. 3A is a graph showing the measurement results of the changes in concentrations of acetaldehyde, acetoin, and methane measured in the atmosphere and in the culture of the DH-1 strain, which was cultured while supplying methane alone, in which (♦) represents methane, (●) represents acetaldehyde, and (▼) represents acetoin.

FIG. 3B is a graph showing the measurement results of the changes in concentrations of acetaldehyde, acetoin, methane, and ethane measured in the atmosphere and in the culture of the DH-1 strain, which was cultured while supplying ethane and methane simultaneously, in which (●) represents methane, (■) represents ethane, (◆) represents acetaldehyde, and (▼) represents acetoin.

FIG. 3C is a graph showing the measurement results of the changes in concentrations of acetaldehyde, acetoin, methane, and ethane measured in the atmosphere and in the culture of the DH-1/2,3-BDO strain, which was cultured while supplying ethane and methane simultaneously, in which (●) represents methane, (■) represents ethane, (◆) represents acetaldehyde, (▼) represents acetoin, and (▲) represents 2,3-butanediol.

FIG. 4A is a graph showing the comparison results of concentrations of succinic acid produced by the DH-1 strain, in a medium.

FIG. 4B is a graph showing the comparison results of concentrations of succinic acid produced by the four kinds of transformed DH-1 strains provided in the present invention, in a medium.

FIG. 5 is a graph showing the comparison results of concentrations of δ-aminolevulinic acid produced by the two kinds of transformed DH-1 strains, in which δ-aminolevulinic acid synthase gene is introduced, in a medium.

FIG. 6 is a graph showing the comparison results of productivity of squalene synthesized in the DH-1 strain and the DH-1/SQU strain cultured for 16 hours and 28 hours, respectively.

FIG. 7A is a graph showing the results comparing 2,3-butanediol production between a wild-type methanotroph and a transformed methanotroph (in which the budABC gene-containing expression vector for methanotrophs was introduced into a wild-type methanotroph (*M. alcaliphilum* strain 20Z)), after culturing the wild-type methanotroph and the transformed methanotroph using methane as a substrate for 96 hours, respectively.

FIG. 7B is a graph showing the results confirming the amounts of acetoin and 2,3-butanediol produced from methane using a transformed methanotroph, after transforming the budABC gene-containing expression vector for methanotrophs into the wild-type methanotroph (*M. alcaliphilum* strain 20Z).

FIG. 7C is a graph showing the results confirming the amount of 2,3-butanediol produced from methane using a transformed methanotroph and cell growth rate thereof, after transforming the budABC gene-containing expression vector for methanotrophs into the wild-type methanotroph (*M. alcaliphilum* strain 20Z).

FIG. 8A is a graph showing the results of quantification analysis with regard to the level of acetoin produced by BL21-pMDHFLS2 (i.e., a transformed *E. coli*), in a medium condition where ethanol and glucose are contained alone or together.

FIG. 8B is a graph showing the results of HPLC analysis with regard to the components contained in the culture product of a transformed *E. coli* capable of expressing MDH and FLS (a recombinant strain producing acetoin) cultured in an ethanol-containing medium, and in the culture product of a transformed *E. coli* capable of expressing MDH, FLS, and bdh1 (a recombinant strain producing 2,3-butanediol), respectively.

BEST MODE

While conducting various studies in an effort to develop a method for more effectively producing metabolites using methanotrophs, the present inventors were interested in a *Methylomonas* sp. DH-1 strain (hereinafter abbreviated as "DH-1 strain"), deposited under Accession Number KCTC18400P. The DH-1 strain, which is a type of methanotroph characterized by efficient biosynthesis of methanol from methane, is a strain that was isolated from sewage sludge and identified by the present inventors, deposited to the Korean Collection for Type Cultures (KCTC) of Korea Research Institute of Bioscience & Biotechnology (KRIBB) on Aug. 27, 2015, and assigned Accession Number KCTC18400P.

The characteristics of the strain were examined using genomes and metabolites of the strain. As a result, it was confirmed that the strain exhibits the following characteristics that: (a) a soluble methane monooxygenase (sMMO) gene is not present; (b) a gene is expressed which is selected from the group consisting of a particulate methane monooxygenase (pMMO) gene, a PQQ-dependent methanol dehydrogenase (mxaFJGIRSACKLDEK) gene, a PQQ biosynthesis gene cluster (pqqBCDE) gene, a pyruvate decarboxylase (PDC) gene, a glutamyl-tRNA synthase (gltX) gene, an NADPH-dependent glutamyl-tRNA reductase (hemA) gene, a glutamate-1-semialdehyde aminotransferase (hemL) gene, a squalene hopene cyclase (shc) gene, and a combination thereof; (c) a pathway is activated which is selected from the group consisting of ribulose monophosphate (RuMP) cycle involved in formaldehyde metabolism, Entner-Doudoroff (ED) pathway, Embden-Meyerhof-Parnas (EMP) pathway, pentose phosphate (PP) pathway, tetrahydromethanopterim ($H_4MPT$) pathway, tetrahydrofolate ($H_4F$) pathway, serine pathway, TCA cycle, C30 carotenoid synthesis pathway, hopanoid biosynthesis pathway, C40 carotenoid synthesis pathway, and a combination thereof; and (d) carbon dioxide is absorbed and fixed by a combination of a pyruvate carboxylase gene, a phosphoenolpyruvate carboxylase gene, and a pyruvate decarboxylase (PDC) gene.

The characteristics confirmed above are those which include the characteristics of type 1 methanotrophs and those of type 2 methanotrophs, and it was confirmed that these characteristics cannot be found in the conventional methanotrophs.

In particular, considering that the TCA cycle and the serine metabolic pathway are activated simultaneously and carbon dioxide can be continuously absorbed during the metabolic process, it was analyzed that the use efficiency of gaseous alkane compounds being introduced from the outside can be increased.

In this regard, the present inventors have confirmed that various metabolites can be produced more effectively by introducing various foreign genes into the DH-1 strain or inhibiting the expression of the endogenous genes therein.

As such, the technique for more effectively producing various metabolites from gaseous alkane compounds using methanotrophs which include the characteristics of both type 1 and type 2 methanotrophs had not been reported previously, but was developed for the first time by the present inventors.

To achieve the above objects, an aspect of the present invention provides a method for producing metabolites from a gaseous alkane compound using a *Methylomonas* sp. DH-1 strain, deposited under Accession Number KCTC18400P, or a transformant thereof.

As used herein, the term "a *Methylomonas* sp. DH-1 strain" refers to a strain derived from sewage sludge and belonging to the genus *Methylomonas* which had not been reported previously, and was deposited to the Korean Collection for Type Cultures (KCTC) of the Korea Research Institute of Bioscience & Biotechnology (KRIBB) on Aug. 27, 2015, and assigned Accession Number KCTC18400P.

In the present invention, the *Methylomonas* sp. DH-1 strain (hereinafter abbreviated as "DH-1 strain") shows the following characteristics:

(a) A soluble methane monooxygenase (sMMO) gene is not present.

(b) A gene is expressed which is selected from the group consisting of a particulate methane monooxygenase (pMMO) gene, a PQQ-dependent methanol dehydrogenase (mxaFJGIRSACKLDEK) gene, a PQQ biosynthesis gene cluster (pqqBCDE) gene, a pyruvate decarboxylase (PDC) gene, a glutamyl-tRNA synthase (gltX) gene, an NADPH-dependent glutamyl-tRNA reductase (hemA) gene, a glutamate-1-semialdehyde aminotransferase (hemL) gene, a squalene hopene cyclase (shc) gene, and a combination thereof.

(c) A pathway is activated which is selected from the group consisting of ribulose monophosphate (RuMP) cycle involved in formaldehyde metabolism, Entner-Doudoroff (ED) pathway, Embden-Meyerhof-Parnas (EMP) pathway, pentose phosphate (PP) pathway, tetrahydromethanopterim ($H_4$MPT) pathway, tetrahydrofolate ($H_4$F) pathway, serine pathway, TCA cycle, C30 carotenoid synthesis pathway, hopanoid biosynthesis pathway, C40 carotenoid synthesis pathway, and a combination thereof.

(d) Carbon dioxide is absorbed and fixed by a combination of a pyruvate carboxylase gene, a phosphoenolpyruvate carboxylase gene, and a pyruvate decarboxylase (PDC) gene.

As used herein, the term "transformant" refers to a engineered strain in which a foreign gene is introduced to a host microorganism and expressed therein or the expression of an endogenous gene of the host microorganism is inhibited so that a genetic characteristic which is different from the original genetic characteristic possessed by the host microorganism can be newly expressed.

In the present invention, the transformant may be interpreted as a modified strain which is capable of producing various metabolites from a gaseous alkane compound, by introducing a foreign gene to a DH-1 strain to be expressed therein or by inhibiting the expression of an endogenous gene thereof.

The DH-1 strain of the present invention or a transformant thereof may be used as a bioreactor that produces metabolites from a gaseous alkane compound.

In particular, as the alkane compound, in an embodiment, a lower alkane compound may be used, and in another embodiment, an alkane compound having 1 to 6 carbon atoms (e.g., methane, ethane, propane, butane, pentane, hexane, etc.) may be used alone or in combination, but the alkane compound is not particularly limited thereto.

Additionally, the metabolites are not particularly limited as long as the metabolites can be produced from a gaseous alkane compound by a DH-1 strain of the present invention or a transformant thereof. In an embodiment, the metabolites may be lower alcohols, TCA cycle components, squalene, aminolevulinic acid, etc.; in another embodiment, lower alcohols, such as methanol, ethanol, propanol, butanol, 2,3-butanediol, pentanol, hexanol, etc.; and in still another embodiment, TCA cycle components, such as succinic acid, oxaloacetate, citric acid, malic acid, succinyl-CoA, etc.

In exemplary embodiments of the present invention, various metabolites were synthesized using the DH-1 strain or a transformant thereof.

In an embodiment, by using a DH-1 strain, ethanol may be produced from gaseous ethane; propanol may be produced from gaseous propane; succinic acid may be produced from gaseous methane; δ-aminolevulinic acid may be produced from gaseous methane; or squalene may be produced from gaseous methane.

In another embodiment, 2,3-butanediol may be produced from gaseous ethane using a transformant where a gene encoding acetoin reductase is introduced into a DH-1 strain; succinic acid may be produced from gaseous methane using a transformant (DH-1/suc:2-B) where a gene encoding succinic acid dehydrogenase (SDH) is deleted in the DH-1 strain; succinic acid may be produced from gaseous methane using a transformant (DH-1/suc:2-A) where a gene encoding isocitrate dehydrogenase is introduced into the transformed DH-1 strain (DH-1/suc:2-B); succinic acid may be produced from gaseous methane using a transformant (DH-1/suc:2-C) where a gene encoding phosphoacetyl transferase (pta) and a gene encoding acetate kinase (ack) are deleted in the transformed DH-1 strain (DH-1/suc:2-A); succinic acid may be produced from gaseous methane using a transformant (DH-1/suc:2-D) where a gene encoding pyruvate formate-lyase (pfl) is deleted in the transformed DH-1 strain (DH-1/suc:2-C); δ-aminolevulinic acid may be produced from gaseous methane using a transformant where a gene encoding δ-aminolevulinic acid synthase is introduced into a DH-1 strain; or squalene may be produced from gaseous methane using a transformant where a gene encoding squalene hopene cyclase is deleted in a DH-1 strain.

The DH-1 strain of the present invention exhibits characteristics which are distinguished from those of conventional methanotrophs in various aspects.

For example, the DH-1 strain is similar to strains of type 1 methanotrophs from the aspect of genomic homology, whereas, reviewing the activated metabolic pathway, the DH-1 strain of the present invention simultaneously exhibits not only the characteristics of type 1 methanotrophs but also those of type 2 methanotrophs. The DH-1 strain can produce a higher level of lower alcohols (e.g., ethanol, propanol, etc.) from lower alkane compounds (e.g., ethane, propane, etc.) in addition to methane, compared to the conventional type 1 methanotrophs. Unlike conventional methanotrophs, DH-1 strain with pyruvate decarboxylase can produce 2,3-butanediol from ethane only by the introduction and expression of the acetoin reductase gene; and these DH-1 strains can not only exhibit their own activity of producing succinic acid from methane without any particular modification, which had not been shown in any kind of methanotrophs that had been reported previously, but can also significantly improve their synthesis efficiency of succinic acid via transformation. In addition, unlike the conventional microorganisms (e.g., *E. coli*, *Corynebacterium*, etc.) in which any one of succinyl-CoA and glycine (i.e., substrates used) must be separately supplied through a medium for the biosynthesis of δ-aminolevulinic acid, the DH-1 strain can synthesize succinyl-CoA and glycine themselves through the activated serine metabolic pathway and TCA cycle, and thus can perform biosynthesis of aminolevulinic acid from methane without the supply of these substrates from the outside. Furthermore, unlike the conventional methanotrophs whose ability of squalene biosynthesis from methane has not been known, the DH-1 strain can not only exhibit the activity of producing squalene from methane, but can also significantly improve the synthesis efficiency of squalene via transformation.

Accordingly, although the DH-1 strain belongs to type 1 methanotrophs, it is shown to be more useful as a bioreactor that produces metabolites using a foreign gaseous alkane as a carbon source, compared to the conventional methanotrophs.

When various metabolites are produced from a gaseous alkane compound using the DH-1 strain of the present invention or a transformant thereof, metabolites produced from the bacterial bodies can be generally recovered. However, on some occasions, these metabolites may also be obtained from the culture product rather than from the bacterial bodies.

The culture product is not particularly limited, and in an embodiment, the culture product may be the culture products, supernatants of the culture, pulverized products, fractions thereof, etc. of the DH-1 strain or a transformant thereof. In another embodiment, the culture product may be the supernatants of the culture obtained by centrifugation of the culture of the DH-1 strain or a transformant thereof, the pulverized product obtained by physical treatment or sonication of the DH-1 strain or a transformant thereof; or fractions obtained by applying methods such as centrifugation, chromatography, etc. to the above culture, supernatants of the culture, pulverized products, etc.

Meanwhile, when various metabolites are produced from a gaseous alkane compound using the DH-1 strain of the present invention or a transformant thereof, the conditions for culturing the DH-1 strain or a transformant thereof may be the concentration of the gaseous alkane compound in the atmosphere, culture temperature, culture time, etc.

Among the above conditions, the concentration of the gaseous alkane compound in the atmosphere is not particularly limited, and in an embodiment, the concentration may be in a range of 10% (v/v) to 80% (v/v), and in another embodiment, in a range of 30% (v/v) to 50% (v/v).

Among the above conditions, the culture temperature is not particularly limited, and in an embodiment, the culture temperature may be in a range of 20° C. to 40° C., and in another embodiment, in a range of 25° C. to 35° C.

Among the above conditions, the culture time is not particularly limited, and in an embodiment, the culture time may be in a range of 10 hours to 300 hours, and in another embodiment, in a range of 16 hours to 200 hours.

In the present invention, the DH-1 strain or a transformant thereof may be cultured using a method well known in the art. Specifically, the culture may be performed continuously in a batch process, fed-batch process, or repeated fed-batch process, but the culture method is not particularly limited thereto as long as various metabolites can be produced from the DH-1 strain or a transformant thereof.

The medium used for the culture may be the nitrate mineral salts (NMS) medium, which is known to be used for the culture of methanotrophs, and a medium in which the components contained in the medium or the content thereof is regulated according to methanotrophs may be used.

Particularly, when the medium contains a salt (e.g., NaCl, KCl, etc.), it is possible to improve the proliferation of the DH-1 strain or a transformant thereof or the productivity of metabolites. In an embodiment, the concentration of the salts contained in the medium may be in a range of 0.1% (w/w) to 3.0% (w/w), in another an embodiment, 1.0% (w/w) to 2.0% (w/w), and in still another embodiment, 1.5% (w/w), but the concentration of the salts is not particularly limited thereto.

Additionally, appropriate precursors for a culture medium may also be used. The above raw materials may be appropriately added to a culture during the culture process by a fed-batch process, batch culture process, or continuous culture process, but the method is not particularly limited thereto. The pH of the culture may be appropriately adjusted using a basic compound (e.g., sodium hydroxide, potassium hydroxide, ammonia, etc.), or an acidic compound (e.g., phosphoric acid, sulfuric acid, etc.).

Additionally, an antifoaming agent (e.g., fatty acid polyglycol ester) may be added to prevent foam generation.

The step of recovering metabolites may be performed by methods known in the art (e.g., dialysis, centrifugation, filtration, solvent extraction, chromatography, crystallization, etc.). For example, the supernatant obtained after removing the DH-1 strain or a transformant thereof by centrifugation of the culture of the DH-1 strain or a transformant thereof may be applied to solvent extraction to recover the desired metabolites.

Additionally, the method to recover these metabolites is not particularly limited, but any method combining known experimental methods according to the characteristics of the desired metabolites may be used as long as the method can recover these metabolites.

DETAILED DESCRIPTION OF THE INVENTION

Hereinafter, the present invention will be described in more detail with reference to the following Examples. However, these Examples are for illustrative purposes only and the scope of the invention is not limited by these Examples.

Example 1: Analysis of Genome and Transcripts of *Methylomonas* sp. DH-1 Strain The present inventors have performed analyses of the genome and transcripts of the *Methylomonas* sp. DH-1 strain (KCTC8400P) (hereinafter abbreviated as "DH-1 strain"), which is a novel strain of methanotrophs registered as a patent through KR Pat. No. 10-1714967, and as a result, they have newly identified the specific characteristics of the DH-1 strain.

First, the present inventors have analyzed the genome of the DH-1 strain (Genbank NZ_CP014360, NZ_CP014361) via DNA-DNA hybridization (DDH), and as a result, they have confirmed that the DH-1 strain includes a 4.86 Mb genomic chromosome and a 278 kb plasmid, in which the entire gene of the DH-1 strain has a sequence homology of 73.9% with that of the *Methylomonas koyamae* Fw12E-YT strain (i.e., a type 1 methanotroph) and the average nucleotide identity (ANI) between the two strains was 97.76%.

Additionally, as a result of analyzing the metabolic pathway using methane based on the DH-1 strain transcripts, it was confirmed that various metabolic pathways distinguished from the conventional type 1 methanotrophs were activated (FIG. 1A).

FIG. 1A is a schematic diagram showing various metabolic pathways activated in the DH-1 strain of the present invention.

As shown in FIG. 1A, with regard to the genes related to C1 metabolism present in normal methanotrophs, it was confirmed that in the DH-1 strain, although the soluble methane monooxygenase (sMMO) gene was not present, both of two copies of particulate methane monooxygenase (pMMO) gene (SEQ ID NO: 1), PQQ-dependent methanol dehydrogenase (mxaFJGIRSACKLDEK) gene, and PQQ biosynthesis gene cluster (pqqBCDE) gene, ribulose monophosphate (RuMP) cycle involved in formaldehyde metabolism, Entner-Doudoroff (ED) pathway, Embden-Meyerhof-Parnas (EMP) pathway, pentose phosphate (PP) pathway, tetrahydromethanopterim (H₄MPT) pathway, and tetrahydrofolate (H₄F) pathway were activated.

Specifically, the DH-1 strain contains all of the serine pathway-related genes known to exist mainly in type 2 methanotrophs and can express phosphoenolpyruvate carboxylase (ppc), and thus is able to convert phosphoenolpyruvate (PEP) to oxaloacetate (OAA) while absorbing carbon dioxide through the ppc and serine metabolic pathways. Additionally, it was confirmed that the TCA cycle, which does not normally function in conventional methanotrophs, functions normally in the DH-1 strain.

According to what has been known thus far, ppc is not expressed in normal type 1 methanotrophs, and thus the serine metabolism pathway does not function normally therein. However, it was confirmed that pyruvate carboxylase, acetyl-CoA carboxylase, and PEP carboxylase as well as ppc are activated in the DH-1 strain, and thus the DH-1 strain can absorb carbon dioxide at a significantly higher level compared to type 1 methanotrophs that have been known thus far.

Additionally, it was confirmed that pyruvate decarboxylase (PDC) (SEQ ID NO: 2), which is not known in type 1 and type 2 methanotrophs, is activated in the DH-1 strain, and thus acetoin (i.e., a precursor of 2,3-butanediol) can be produced when ethane is supplied.

Furthermore, it was confirmed that a metabolic pathway is activated by which secondary metabolites are synthesized using the geranyl pyrophosphate (GPP) produced by MET pathway (FIG. 1B).

FIG. 1B is a schematic diagram showing a metabolic pathway for synthesizing secondary metabolites activated in the DH-1 strain of the present invention.

As shown in FIG. 1B, it was confirmed that the GPP produced by the MEP pathway can produce various secondary metabolites via various synthesis pathways (e.g., C30 carotenoid synthesis pathway, hopanoid biosynthesis pathway, C40 carotenoid synthesis pathway, etc.).

In addition, the expression of a gene encoding glutamyl-tRNA synthase (gltX) (SEQ ID NO: 4), a gene encoding NADPH-dependent glutamyl-tRNA reductase (hemA) (SEQ ID NO: 5), a gene encoding glutamate-1-semialdehyde aminotransferase (hemL) (SEQ ID NO: 6), a gene encoding squalene hopene cyclase (shc) (SEQ ID NO: 9), etc. was confirmed.

As such, the DH-1 strain provided in the present invention appears to be similar to type 1 methanotrophs from the aspect of genome homology. However, reviewing the activated metabolic pathways, it was confirmed that the DH-1 strain simultaneously exhibited the characteristics of both type 1 and type 2 methanotrophs.

Accordingly, the analysis revealed that as a bioreactor producing metabolites using a gaseous alkane from the outside, the DH-1 strain is superior to any kind of methanotrophs known thus far.

Example 2: Alcohol Biosynthesis Using *Methylomonas* Sp. DH-1 Strain

In the biosynthesis of alcohols (e.g., ethanol, propanol, etc.) using methanotrophs from lower alkanes such as ethane or propane other than methane, the performance of the DH-1 strain was evaluated. In particular, the *Methylomicrobium alcaliphilum* 20Z strain (i.e., a type 1 methanotroph) was used as the control strain.

Specifically, the control strain and the DH-1 strain were each inoculated into a nitrate mineral salt (NMS) medium containing a race elements solution (1,000×), phosphate stock solution (100×), and vitamin stock (100×), and cultured to the same concentration (2.4 g DCW/L). Thus-obtained cultures of each strain were suspended in sodium phosphate buffer (pH 7.0) to obtain a suspension for each strain. Then, 40 mM formate and 0.5 mM EDTA were added to each suspension to inhibit the activity of methanol dehydrogenase (MDH) of each strain. In particular, the composition of the trace elements solution (1,000×) was set to contain $FeSO_4 \cdot 7H_2O$ (500 mg/L), $ZnSO_4 \cdot 7H_2O$ (400 mg/L), $MnCl_2 \cdot 7H_2O$ (20 mg/L), $CoCl_2 \cdot 6H_2O$ (50 mg/L), $NiCl_2 \cdot 6H_2O$ (10 mg/L), $H_3BO_3$ (15 mg/L), and EDTA (250 mg/L); and the composition of the phosphate stock solution (100×) was set to contain $KH_2PO_4$ (26 g/L) and $Na_2HPO_4 \cdot 7H_2O$ (62 g/L); the vitamin stock (100×) was set to contain biotin (2 mg/L), folic acid (2 mg/L), thiamine HCl (5 mg/L), Ca pantothenate (5 mg/L), vitamin $B_{12}$ (0.1 mg/L), riboflavin (5 mg/L), and nicotinamide (5 mg/L); and the NMS medium was set to contain $MgSO_4 \cdot 7H_2O$ (1 g/L), $KNO_3$ (1 g/L), $CaCl_2 \cdot H_2O$ (0.2 g/L), Fe-EDTA (0.0038 g/L), and $NaMo \cdot 4H_2O$ (0.0005 g/L).

Then, each suspension was added into a sealed container, and 30% (v/v) ethane (or propane) was added thereto. While reacting the mixture at a rate of 230 rpm at 30° C. for 16 hours, samples were aliquoted at time-points of 1, 2, 4, and 16 hours after the reaction started. Each aliquoted sample was heated at 90° C. for 30 minutes to inactivate each strain contained in each sample, cooled to 4° C., and centrifuged to obtain the supernatant. The concentration of ethanol and propanol contained in the supernatant was measured (FIGS. 2A and 2B). In particular, the concentration of the ethanol and propanol was analyzed using a Younglin 6500® gas chromatograph (GC) equipped with an HP-Plot Q capillary tube and a thermal conductivity detector. For the analysis, nitrogen was used as mobile phase, and the flow rate was set at 2 mL/min and the injection volume was 10 μL. The GC oven temperature was initially maintained at 100° C. for 1 minute, increased to 170° C. at 10° C./min, and then held at 170° C. for 1 minute. The temperatures for the injector and detector were 250° C. and 230° C., respectively. For the analysis of ethanol and 2-propanol, a flame ionization detector (FID) was used. The temperatures for the injector and detector were maintained at 250° C. and the oven temperature was maintained at 60° C. for 0.5 minutes, increased to 260° C. at a rate of 20° C./min, and then held at 260° C. for 5 minutes.

FIG. 2A is a graph showing the comparison results of the concentrations of ethanol produced by the control strain and the DH-1 strain of the present invention.

As shown in FIG. 2A, it was confirmed that the control strain did not produce ethanol from ethane at all, whereas the DH-1 strain produced ethanol from ethane at a certain level (max. concentration: 0.11 g/L; and max. productivity: 0.025 g/L/h).

FIG. 2B is a graph showing the comparison results of the concentrations of propanol produced by the control strain and the DH-1 strain of the present invention.

As shown in FIG. 2B, it was confirmed that the control strain produced propanol from propane at a low concentration (0.1 g/L or less), whereas the DH-1 strain produced propanol at a relatively high level (max. concentration: 0.272 g/L; and max. productivity: 2.566 gig DCW).

The lower alcohols, such as ethanol and propanol, are a primary metabolite synthesized using a gaseous alkane from the outside by particulate methane monooxygenase (pMMO) expressed in type 1 methanotrophs, and the productivity of these lower alcohols may serve as a major criterion for evaluating the performance of methanotrophs as a bioreactor.

As shown in FIGS. 2A and 2B, it was analyzed that the DH-1 strain, whose characteristics were newly identified in the present invention, was found to be superior to the conventional type 1 methanotrophs with regard to the ability of alcohol biosynthesis using a gaseous alkane from the outside. As a result of the analysis whether or not an enzyme other than pMMO was expressed in the above DH-1 strain, it was confirmed that only a gene cluster encoding pMMO (pmmoBAC, SEQ ID NO: 1) was expressed similar to the conventional type 1 methanotrophs.

Accordingly, it was again confirmed that while the DH-1 strain belongs to type 1 methanotrophs, it exhibits its superiority as a bioreactor producing metabolites using a gaseous alkane from the outside as a carbon source.

Example 3: Biosynthesis of 23-Butanediol (23-BDO) Using *Methylomonas* sp. DH-1 Strain Example 3-1: Confirmation of Acetoin-Producing Ability of DH-1 Strain Since natural gas contains various impurities such as ethane and propane in addition to methane as the main component, an attempt was made to utilize methane as a carbon source for cell growth via simultaneous conversion of methane and ethane using a DH-1 strain while utilizing ethane as a substrate for producing metabolites.

First, the DH-1 strain was inoculated into an NMS medium and cultured for 200 hours under atmospheric conditions containing methane (20) and air (80%), and the changes in the concentrations of acetaldehyde and acetoin contained in the medium aliquoted during the culture process and the methane concentration in the atmosphere were analyzed (FIG. 3A).

FIG. 3A is a graph showing the measurement results of the changes in concentrations of acetaldehyde, acetoin, and methane measured in the atmosphere and in the culture of the DH-1 strain, which was cultured while supplying methane alone, in which (♦) represents methane, (●) represents acetaldehyde, and (▼) represents acetoin.

As shown in FIG. 3A, it was confirmed that with the progress of culture time, the methane concentration in the atmosphere decreased and the cell number of the microorganism increased, but the acetaldehyde concentration and acetoin concentration (0.038 mmol) did not change.

Therefore, it was confirmed that most of the methane supplied while culturing the DH-1 strain was used as a carbon source for the growth of the cells.

Then, the DH-1 strain was inoculated into an NMS medium and cultured for 200 hours under atmospheric conditions containing methane (20%), ethane (10%), and air (70%), and the changes in the concentrations of acetaldehyde and acetoin contained in the medium aliquoted during the culture process and the methane concentration in the atmosphere were analyzed (FIG. 3B).

FIG. 3B is a graph showing the measurement results of the changes in concentrations of acetaldehyde, acetoin, methane, and ethane measured in the atmosphere and in the culture of the DH-1 strain, which was cultured while supplying ethane and methane simultaneously, in which (●) represents methane, (■) represents ethane, (♦) represents acetaldehyde, and (▼) represents acetoin.

As shown in FIG. 3B, it was confirmed that with the progress of culture time, the methane and ethane concentrations in the atmosphere decreased and the acetoin concentration increased, thereby showing a maximum concentration of 0.322 mmol.

According to the analysis results of genome and transcripts performed in Example 1, it was confirmed that the ethane in the atmosphere was first converted to ethanol and acetaldehyde by pMMO and methanol dehydrogenase (MDH) and then converted to acetoin by pyruvate decarboxylase (PDC) (SEQ ID NO: 2).

Example 3-2: Preparation of Transformed DH-1 Strain in which Acetoin Reductase Gene is Introduced and Biosynthesis of 2,3-Butanediol (2,3-BDO) Using the Transformed DH-1 Strain To produce 2,3-butanediol in a DH-1 strain using ethane, a vector for introducing a gene encoding acetoin reductase derived from *Klebsiella pneumonia* (SEQ ID NO: 3) into the DH-1 strain was prepared as follows.

First, PCR amplification was performed using the pAWP89 vector as a template along with the primers shown below.

```
pAWP89 vector FP:
                                    (SEQ ID NO: 10)
5'-TAGTTGTCGGGAAGATGCGT-3' pAWP89 vector RP:
                                    (SEQ ID NO: 11)
5'-AGCTGTTTCCTGTGTGAATA-3'
```

Additionally, for the amplification of budABC gene cluster from the gDNA of a *K. pneumonia* strain, PCR amplification was performed using the gDNA as a template along with the primers shown below.

```
budABC_FP:
                                    (SEQ ID NO: 12)
5'-TTCACACAGGAAACAGCTATGAATCATTCTGCTGAATGCACC-3' budABC_RP:
                                    (SEQ ID NO: 13)
5'-GCATCTTCCCGACAACTATTAGTTAAACACCATGCCGCC-3'
```

Then, each of the amplified fragments was ligated to prepare a recombinant vector pAWP89-kleb-budABC.

PCR amplification was performed using the prepared pAWP89-kleb-budABC as a template along with the primers shown below. The obtained fragments were processed using DpnI, antarctic phosphatase, T4 polynucleotide kinase, and T4 ligase to prepare pAWP89-kleb-budC.

```
Kleb-budC FP:
                                    (SEQ ID NO: 14)
5'-aggaaagaaaaatgaaaaaagtcgcacttgt-3'

Kleb-budC RP:
                                    (SEQ ID NO: 15)
5'-tattgtgatgacCCACACATTATACGAGCCGA-3'
```

Meanwhile, for the introduction of acetoin reductase gene at the position of the glycogen synthase (GS) gene present in the genome of the DH-1 strain, a deletion vector, pCM351_GS, was first prepared.

Accordingly, PCR amplification was performed using a 1,000 bp gene fragment corresponding to an upstream region of the GS gene (GS_A region) as a template along with the primers shown below.

```
A region_FP:
                                  (SEQ ID NO: 16)
5'-aattggtaccCAAAATTCGCAGAATATCCT-3'

A region_RP:
                                  (SEQ ID NO: 17)
5'-CGGTAATACGGGCGGTTTGCCTGGCGCTGG-3'
```

Additionally, PCR amplification was performed using a 1,000 bp gene fragment corresponding to a downstream region of the GS gene (GS_B region) as a template along with the primers shown below.

```
B region_FP
                                  (SEQ ID NO: 18)
5'-gttaaccggtGTGGCAAATTACATTTTCAA-3'

B region_RP
                                  (SEQ ID NO: 19)
5'-tagtgagctcTCTGGCTGGAGGAATTCCAT-3'
```

The amplified upstream fragment and downstream fragment were ligated to prepare a deletion vector, pCM351-GS.

PCR amplification was performed using the pCM351-GS deletion vector as a template along with the primers shown below.

```
351_RP:
                                  (SEQ ID NO: 20)
5'-CGGTAATACGGGCGGTTTGCCTGGCGCTGG-3'

351_FP:
                                  (SEQ ID NO: 21)
5'-GATGCGTGATatggatgcatatggcggccg-3'
```

PCR amplification was performed using the prepared pAWP89-kleb-budC as a template along with the primers shown below.

```
tac budC FP:
                                  (SEQ ID NO: 22)
5'-GCAAACCGCCCGTATTACCGCCTTTGAGTG-3' tac budC RP:
                                  (SEQ ID NO: 23)
5'-atgcatccatATCACGCATCTTCCCGACAA-3'
```

The amplified product of the pCM35 I-GS deletion vector and the amplified product of the pAWP89-kleb-budC were ligated to prepare a recombinant vector, pCM351-GS::budC, GenR.

The prepared recombinant vector pCM351-GS::budC, GenR was introduced into a DH-1 strain by electro transformation and stabilized by culturing in an NMS medium for 16 hours. The culture was plated on an NMS solid medium containing gentamicin and cultured for one week to induce double crossover homologous recombination, and thereby a transformed DH-1 strain (DH-1/2,3-BDO) was prepared.

The prepared DH-1/2,3-BDO was inoculated into an NMS medium and cultured for 200 hours under atmospheric conditions containing methane (20%), ethane (10%), and air (70%), and the changes in the concentrations of acetaldehyde and acetoin contained in the medium aliquoted during the culture process and the methane concentration in the atmosphere were analyzed (FIG. 3C).

FIG. 3C is a graph showing the measurement results of the changes in concentrations of acetaldehyde, acetoin, methane, and ethane measured in the atmosphere and in the culture of the DH-1/2,3-BDO strain, which was cultured while supplying ethane and methane simultaneously, in which (●) represents methane, (■) represents ethane, (♦) represents acetaldehyde, (▼) represents acetoin, and (▲) represents 2,3-butanediol.

As shown in FIG. 3C, it was confirmed that with the progress of culture time, the methane concentration in the atmosphere decreased while the 2,3-butanediol concentration decreased. In particular, it was confirmed that the maximum concentration of 2,3-butanediol was 0.237 mmol.

According to what has been known thus far, for biosynthesis of 2,3-BDO from methane using a microorganism, it is necessary to prepare a transformant in which genes encoding all of methane monooxygenase, methanol dehydrogenase, α-acetolactate synthase, α-acetolactate decarboxylase, and acetoin reductase are introduced so that these proteins can be co-expressed; or even when a methanotroph is used as a host cell, it is necessary to prepare a transformant in which genes encoding all of, aldehyde lyase, and acetoin reductase are introduced so that these proteins can be co-expressed.

However, it was confirmed that when the DH-1 strain is used as a host cell, 2,3-butanediol can be synthesized from ethane by introducing only a gene encoding acetoin reductase, and this can prevent the loss of carbon sources in the form of carbon dioxide in the biosynthesis pathway of 2,3-butanediol, and thus the DH-1 strain has a significant advantage over the technologies using methanotrophs as well as conventional microorganisms.

Example 4: Biosynthesis of Succinic Acid Using *Methylomonas* Sp. DH-1 Strain

Example 4-1: Production of Succinic Acid in DH-1 Strain

A DH-1 strain was inoculated into an NMS medium. While culturing the DH-1 strain at 30° C. at a rate of 230 rpm in the atmosphere, culture samples were aliquoted at intervals of 24 hours and the concentration of succinic acid contained therein was analyzed (FIG. 4). In particular, the concentration of succinic acid was analyzed by HPLC using an Aminex HPX-87H column, in which a refractive index (RI) detector was used and 5 mM $H_2SO_4$ was flowed onto the column at a rate of 0.7 mL/min.

FIG. 4 is a graph showing the comparison results of concentrations of succinic acid produced from the DH-1 strain in a medium.

As shown in FIG. 4, it was confirmed that when the DH-1 strain is cultured for 7 days, succinic acid can be produced in a maximum amount of 9.53 mg/L.

Example 4-2: Preparation of Transformed DH-1 Strain for Production of Succinic Acid For more efficient production of succinic acid, 4 kinds of transformed DH-1 strains were prepared.

The first transformed DH-1 strain was prepared as follows:

First, the restriction sites on which restriction enzymes present in the multiple cloning site of the pCM184 vector (Addgene Plasmid #46012) act were cleaved with EcoRI and SacI.

Then, PCR amplification was performed using, as a template, a 666 bp gene fragment corresponding to an upstream region of the SDH gene cassette included in the genome of the DH-1 strain (flank-1-SDH), along with the primers shown below.

```
Flank 1-SDH-For:
                                (SEQ ID NO: 24)
5'-acctgacgtctagatctgGTTCCGCTTGATGGGCTTTG-3'

Flank 1-SDH-Rev:
                                (SEQ ID NO: 25)
5'-gtaccaattgtacagctgGCGGTAAACCTGCAAATGGG-3'
```

Additionally, PCR amplification was performed using, as a template, a 574 bp gene fragment corresponding to a downstream region of the SDH gene cassette included in the genome of the DH-1 strain (flank-2-SDH), along with the primers shown below.

```
Flank 2-SDH-For:
                                (SEQ ID NO: 26)
5'-cgtgttaaccggtgagctATCAGCGACTACCAAGGCAC-3'

Flank 2-SDH-Rev:
                                (SEQ ID NO: 27)
5'-tggatcctctagtgagctGTTGCAGACAGATAAGCGCG-3'
```

The amplified upstream fragment and the amplified downstream fragment were ligated to the cleaved pCM184 to prepare the deletion vector, pCM184-SDH.

The prepared deletion vector, pCM184-SDH, was introduced into a DH-1 strain by electro transformation and stabilized by culturing in an NMS solid medium for 16 hours. The culture was plated on an NMS medium containing kanamycin or gentamicin and cultured for one week to induce double crossover homologous recombination, and thereby a transformed DH-1 strain (DH-1/suc:2-B) was prepared.

The second transformed DH-1 strain was prepared as follows:

The genes encoding isocitrate lyase and malate synthase present on the genome of *E. coli* MG1655 were cloned, and a ribosome binding site acting on the *Methylomonas* sp. DH-1 was inserted into an upstream region of the sequence encoding each enzyme, and the mxaF promoter of the *Methylomonas* sp. was inserted into an upstream region of the cluster to which isocitrate lyase and malate synthase are attached, and thereby the cluster sequence was obtained.

PCR amplification was performed using the prepared cluster sequence as a template along with the primers shown below.

```
Cluster-For:
                                (SEQ ID NO: 28)
5'-cagctgtacaattggtacAGGCAATACTTCCTCTTTCGC-3'

Cluster-Rev:
                                (SEQ ID NO: 29)
5'-catatgcatccatggtacTTAGAACTGCGATTCTTCAGTGGA-3'
```

The gene fragment obtained by PCR amplification was inserted into the pCM184-SDH deletion vector, which was cleaved with Kpn1, to prepare a recombinant vector, pCM184-SDH::-ISL-MS.

The prepared recombinant vector, pCM184-SDH::-ISL-MS, was introduced into a DH-1 strain by electro transformation and stabilized by culturing in an NMS medium for 16 hours. The culture was plated on an NMS solid medium containing kanamycin or gentamicin and cultured for one week to induce double crossover homologous recombination, and thereby a transformed DH-1 strain (DH-1/suc:2-A) was prepared.

The third transformed DH-1 strain was prepared as follows:

To delete the phosphoacetyl transferase (pta) gene included in the genome of the DH-1 strain. PCR amplification was performed using the pCM351 vector as a template along with the primers shown below.

```
Flank 2-pta-For:
                                (SEQ ID NO: 30)
5'-CGTGTTAACCGGTGAGCTATGTCTTGGGCAAAACAGGC-3'

Flank 2-pta-Rev:
                                (SEQ ID NO: 31)
5'-TGGATCCTCTAGTGAGCTAAAACTCGTCGGTGGTGTTG-3'
```

Additionally, to delete the acetate kinase (ack) gene included in the genome of the DH-1 strain, PCR amplification was performed using the pCM351 vector as a template along with the primers shown below.

```
Flank 1-ack-For:
                                (SEQ ID NO: 32)
5'-ACCTGACGTCTAGATCTGCCGAAAGATTGGCTGCTGAT-3'

Flank 1-ack-Rev:
                                (SEQ ID NO: 33)
5'-GTACCAATTGTACAGCTGAAAATACATCGGCGCCTACT-3'
```

The two gene fragments obtained via each PCR amplification above were cloned into the recombinant vector, pCM184-SDH::-ISL-MS, and isocitrate lyase gene and malate synthase gene were ligated thereto, and thereby a vector for deleting acetate production pathway, pCM351-ack-pta, was prepared.

The prepared deletion vector, pCM351-ack-pta, was introduced into the DH-1/suc:2-A strain (i.e., the secondly-prepared DH-1 strain) by electro transformation and stabilized by culturing in an NMS medium for 16 hours. The culture was plated on an NMS solid medium containing kanamycin or gentamicin and cultured for one week to induce double crossover homologous recombination, and thereby a transformed DH-1 strain (DH-1/suc:2-C) was prepared.

The fourth transformed DH-1 strain was prepared as follows:

To delete the pyruvate formate-lyase (pfl) gene included in the genome of the DH-1 strain, the multiple cloning site of the pCM351 was cleaved with EcoRI and SacI.

Then, PCR amplification was performed using, as a template, a gene fragment corresponding to an upstream region of the pfl gene cassette included in the genome of the DH-1 strain (flank-1-pfl) along with the primers shown below.

```
Flank 2-pfl-For:
                                (SEQ ID NO: 34)
5'-acctgacgtctagatagGCCGCTTTCACCATTTCCTT-3'

Flank 2-pfl-Rev:
                                (SEQ ID NO: 35)
5'-gtaccaattgtacagctgCGATGAAAATCTGCGCGGTAG-3'
```

Additionally, PCR amplification was performed using, as a template, a gene fragment corresponding to a downstream region of the pfl gene cassette included in the genome of the DH-1 strain (flank-1-pfl) along with the primers shown below.

Flank 1-pfl-For:
(SEQ ID NO: 36)
5'-cgtgttaaccggtgagcaTCTACCGAAATACCGCCGT-3'

Flank 1-pfl-Rev:
(SEQ ID NO: 37)
5'-tggatcctctagtgagctAACCACGCCGAAAACCTAAC-3'

The two gene fragments obtained via each PCR amplification above were recombined to prepare a deletion vector, pCM351-PFL::GenR.

The prepared deletion vector, pCM351-PFL::GenR, was introduced into the DH-1/suc:2-A strain (i.e., the secondly-prepared DH-1 strain) by electro transformation and stabilized by culturing in an NMS medium for 16 hours. The culture was plated on an NMS solid medium containing gentamicin and cultured for one week to induce double crossover homologous recombination, and thereby a transformed DH-1 strain (DH-1/suc:2-D) was prepared.

Example 4-3: Verification of Two Transformed DH-1 Strains

Among the 4 kinds of transformed DH-1 strains prepared in Example 4-2, the success of transformation of DH-1/suc:2-A and DH-1/suc:2-B strains were verified based on the activities of isocitrate lyase and malate synthase (Table 1).

First, the activity of isocitrate lyase was calculated as follows: 8 mM isocitrate was added to a reaction mixture (A), which consisted of 100 mM potassium phosphate (pH 7.0), 6 mM $MgCl_2$, 4 mM phenylhydrazine hydrochloride, 12 mM L-cysteine hydrochloride, and an extract of the DH-1/suc:2-A strain or DH-1/suc:2-B strain (50 gig to 200 µg), and the changes in absorbance of the resulting product (i.e., glyoxylate phenylhydrazone) at 324 nm were measured.

Then, the activity of malate synthase was calculated as follows: glyoxylate (final concentration: 0.5 mM) was added to a reaction mixture (B), which consisted of 90 mM Tris (pH 8.0), 3.4 mM $MgCl_2$, 0.05 mM acetyl-CoA (sodium salt), and an extract of the DH-1/suc:2-A strain or DH-1/suc:2-B strain (100 µg), and as the sulfur-ester bond of the acetyl-CoA became decomposed, the changes in absorbance of the resulting product (i.e., glyoxylate phenylhydrazone) at 232 nm were measured.

TABLE 1

Analysis of activities of isocitrate lyase and malate synthase

| Strain | Activity of Isocitrate Lyase | Activity of Malate Synthase |
|---|---|---|
| DH-1 Strain | ND | ND |
| DH-1/suc:2-A Strain | 7203 ± 216 | 10370 ± 419 |
| DH-1/suc:2-B Strain | ND | ND |

As shown in Table 1, the activities of isocitrate lyase and malate synthase were not detected in the DH-1 strain and the DH-1/suc:2-B strain, in which isocitrate lyase gene and malate synthase gene were not introduced, whereas the activities of isocitrate lyase and malate synthase were detected in the DH-1/suc:2-A, in which isocitrate lyase gene and malate synthase gene were introduced. Therefore, the analysis revealed that the DH-1/suc:2-A strain was prepared normally.

Example 4-4: Analyses of Cell Growth and Succinic Acid Productivity of Four Transformed DH-1 Strains Cell growth and succinic acid productivity were analyzed in the four kinds of transformed DH-1 strains prepared in Example 4-2.

First, the four kinds of transformed DH-1 strains were each inoculated into an NMS medium. While culturing these four kinds of strains in the atmosphere containing methane (30%) at 30° C. and at a rate of 230 rpm, the absorbance of each culture was measured at intervals of 24 hours and the concentration of cell bodies of each culture was analyzed, and thereby the cell growth level was analyzed.

Additionally, each of the four kinds of transformed DH-1 strains was inoculated into an NMS medium. While culturing each strain in the atmosphere containing methane at 30° C. and at a rate of 230 rpm, samples of each culture were aliquoted at intervals of 24 hours and the concentration of succinic acid contained therein was analyzed (FIG. 4). In particular, the concentration of succinic acid was analyzed by HPLC using an Aminex HPX-87H column, in which a refractive index (RI) detector was used and 5 mM $H_2SO_4$ was flowed onto the column at 60° C. at a rate of 0.7 mL/min.

FIG. 4B is a graph showing the comparison results of concentrations of succinic acid produced from the four kinds of transformed DH-1 strains provided in the present invention in a medium.

As shown in FIG. 4B, the maximum amount of succinic acid produced by the DH-1/suc:2-B strain was 95.0 mg/L and the maximum amount of succinic acid produced by the DH-1/suc:2-A strain was 134.48 mg/L, thus showing a 14.1-fold improvement in succinic acid productivity compared to the DH-1 strain.

The DH-1/suc:2-C strain (99.76 mg/mL) and the DH-1/suc:2-D strain (92.0 mg/mL), in which the succinic acid production pathway and competing pathway were deleted, showed a similar level of succinic acid productivity up to day 8. Thereafter, the DH-1/suc:2-D strain showed a decrease in the productivity of succinic acid while maintaining the concentration of cell bodies.

Taken together, the DH-1 strain of the present invention has advantages in that the strain not only exhibits activity of producing succinic acid from methane, which has not been shown in any of the previously reported methanotrophs, but also significantly improves the synthesis efficiency of succinic acid by transformation.

Example 5: Biosynthesis of Aminolevulinic Acid Using *Methylomonas* sp. DH-1 Strain

Example 5-1: Verification of Ability to Biosynthesize Aminolevulinic Acid by DH-1 Strain A DH-1 strain and a type 1 methanotroph (*Methylomicrobium alcaliphilum* 20Z), and a type 2 methanotroph (*Methylosinus trichosporium* OB3b) were each inoculated into an NMS medium ($MgSO_4·7H_2O$ (1 g/L), $KNO_3$ (1 g/L), $CaCl_2·H_2O$ (0.2 g/L), Fe-EDTA (0.0038 g/L), and $NaMo·4H_2O$ (0.0005 g/L)), and cultured in the atmosphere containing methane (30% (v/v)) at 30° C. and at a rate of 230 rpm for 120 hours.

After completion of the culture, the culture supernatant of each strain was obtained and the concentration of aminolevulinic acid contained in the culture supernatant was measured. In particular, the concentration of aminolevulinic acid was measured as follows. The culture supernatant (2 mL) and 1.0 M sodium acetate (pH 4.6; 1 mL) were mixed and acetylacetone (0.5 mL) was added thereto to obtain a mixture. Then, the mixture was heated at 100° C. for 15 minutes and cooled for 15 minutes. The cooled mixture (2 mL) and the Ehrlich reagent (2 mL) were mixed and reacted, and the absorbance of the resulting product was measured at 554 nm.

As a result, aminolevulinic acid (about 2.19 mg/L) was detected in the culture supernatant obtained by culturing the DH-1 strain for 120 hours, whereas only a trace amount of aminolevulinic acid was detected in each of the type 1 methanotroph (*Methylomicrobium alcaliphilum* 20Z) and the type 2 methanotroph (*Methylosinus trichosporium* OB3b).

Accordingly, it was confirmed that the DH-1 strain can biosynthesize aminolevulinic acid via the C5 pathway, and also that the biosynthesis efficiency of the DH-1 strain is superior to those of conventional methanotrophs.

Example 5-2: Preparation of Transformed DH-1 Strain in which Aminolevulinic Acid Synthase (ALAS) Gene is Introduced Since the DH-1 strain cannot express the aminolevulinic acid synthase involved in the C4 pathway, aminolevulinic acid cannot be biosynthesized through the C4 pathway. In this regard, an attempt was made to examine whether or not aminolevulinic acid can be biosynthesized through the C4 pathway when aminolevulinic acid synthase is expressed in the DH-1 strain by introducing the aminolevulinic acid synthase gene into the DH-1 strain.

First, as the aminolevulinic acid synthase gene to be introduced, the aminolevulinic acid synthase gene derived from a type 2 methanotroph (*Methylosinus trichosporium* OB3b) (OB-ALAS, SEQ ID NO: 7) and the aminolevulinic acid synthase gene derived from *Rhodobacter* sp. (Rs_ALAS, SEQ ID NO: 38) were each synthesized.

Then, the replication origin derived from the DH-1 strain and a nucleotide sequence encoding a DNA binding protein were inserted into the pAWP78 vector to prepare a pDH shuttle vector.

Inverse PCR amplification was performed using the prepared pDH shuttle vector as a template along with the primers shown below.

```
                                          (SEQ ID NO: 40)
DH_inverse_FP: 5'-CAAtaaggatcccaggcatc-3'

(SEQ ID NO: 41)
DH_inverse: RP: 5'-CCATATGAGATctcctttaacag-3'
```

Then, PCR amplification was performed using the synthesized OB-ALAS as a template along with the primers shown below.

```
OB3bALAS_FP:
                                          (SEQ ID NO: 42)
5'-gttaaaggagATCTCATATGGATTACCGGCGCTTTTCGAGACGG-

3'

OB3bALAS_RP:
                                          (SEQ ID NO: 43)
5'-gatgcctggggatccttaTTGCGCGGCGAGCTTGATCTCGGGATAG-

3'
```

Additionally. PCR amplification was performed using the synthesized Rs_ALAS as a template along with the primers shown below.

```
RsALAS_FP:
                                          (SEQ ID NO: 44)
5'-cacatacactgttaaaggagATCTCATATGGACTACAACTTGGCCTT

GGACACCGC-3'

RsALAS_RP:
                                          (SEQ ID NO: 45)
5'-cgttttatttgatgcctggggatccTCAGGCGACGACTTCGGCGCGG

TTCAAG-3'
```

The OB-ALAS was introduced into the amplified pDH shuttle vector to prepare the DH-1 shuttle vector_OB3bALAS recombinant vector, and the Rs_ALAS was introduced into the amplified pDH shuttle vector to prepare the DH-1 shuttle vector_RsALAS recombinant vector.

The prepared DH-1 shuttle vector_OB3bALAS recombinant vector and DH-1 shuttle vector_RsALAS recombinant vector were each introduced into the DH-1 strain by electro transformation and stabilized by culturing in an NMS medium for 16 hours. Each culture was plated on an NMS solid medium containing kanamycin and cultured for one week to induce double crossover homologous recombination, and thereby the respective transformed DH-1 strains, DH-1 (OB3bALAS) and DH-1 (RsALAS), were prepared.

To verify the success of transformation of the prepared DH-1(OB3bALAS) and DH-1(RsALAS), colony PCR was first performed, and thereby success of transformation was confirmed.

Additionally, each transformed DH-1 strain was cultured and total RNA was obtained therefrom, and reverse transcription was performed to obtain cDNA thereof. The cNDA was amplified and the success of transformation was verified again.

Example 5-3: Analysis of Productivity of Aminolevulinic Acid Produced in Transformed DH-1 Strain A DH-1 strain, a DH-1 (OB3bALAS), and a DH-1 (RsALAS) were each inoculated into an NMS medium and cultured in the atmosphere containing methane (30% (v/v)) at 30° C. and at a rate of 230 rpm for 120 hours. After completion of the culture, the culture supernatant of each strain was obtained and the concentration of aminolevulinic acid contained in the culture supernatant was measured (FIG. 5).

FIG. 5 is a graph showing the comparison results of aminolevulinic acid productivity represented by the two kinds of transformed DH-1 strains in which aminolevulinic acid synthase gene was introduced.

As shown in FIG. 5, the transformed DH-1 strains showed relative superiority in aminolevulinic acid productivity compared to the DH-1 strain, and with the progress of culture time, the difference in aminolevulinic acid productivity was further increased. Simply, when cultured for 120 hours, the DH-1 strain produced about 2.19 mg/L of aminolevulinic acid while the transformed DH-1 strains produced aminolevulinic acid in a range of about 3.78 mg/L to about 3.94 mg/L, thus confirming that the transformed DH-1 strains have 1.8-fold increased aminolevulinic acid productivity compared to those of the DH-1 strains.

Conventionally, for the biosynthesis of aminolevulinic acid via the C4 pathway, succinyl-CoA and glycine are required as a substrate. The conventional methanotrophs, in which the serine pathway supplying glycine and the TCA cycle supplying succinyl-CoA are not co-activated, there is a disadvantage in that aminolevulinic acid can be biosynthesized via the C4 pathway only when one of the two substrates must be supplied from the outside.

However, the serine pathway and the TCA cycle are co-activated in the transformed DH-1 strains provided in the present invention, in which aminolevulinic acid synthase gene is introduced, and thus, aminolevulinic acid can be biosynthesized using methane as a sole carbon source even if succinic acid or glycine is not supplied from the outside. This advantage was confirmed to be a novel characteristic of the transformed DH-1 strains, which has not been shown in conventional methanotrophs.

Example 6: Biosynthesis of Squalene Using *Methylomonas* Sp. DH-1 Strain

It was confirmed that the DH-1 strain can biosynthesize squalene from methane, and an attempt was made to determine whether or not squalene productivity can be improved by the inhibition of squalene hopene cyclase (Shc), which is expressed in the DH-1 strain.

Example 6-1: Preparation of Transformed DH-1 Strain where she Expression is Inhibited To remove the gene encoding the Shc protein (SEQ ID NO: 9), which is expressed in the Shc DH-1 strain, the Cre-lox system was used.

Briefly, the upstream sequence of the Shc gene (SEQ ID NO: 46) was cloned using the following primers between the restriction enzyme sites for EcoRI and KpnI present in the lox loci of the pCM184 vector.

```
DH-1_upstream_EcoRI (Forward):
                                                (SEQ ID NO: 47)
5'-ACGTCTAGATCTGAATTCCATCTCGGCCGGGTCGGCAATAGC-3'

DH-1_upstrearn_KpnI (Reverse):
                                                (SEQ ID NO: 48)
5'-ATATGCATCCATGGTACCCGTGAGTTGCGGAATCGTCG-3'
```

Additionally, the downstream sequence of the Shc gene (SEQ ID NO: 49) was cloned using the following primers between the restriction enzyme sites for MluI and SacI present in the lox loci of the pCM184 vector, and thereby a vector for deletion of Shc gene was prepared.

```
  DH-1_downstream_MluI (Forward):
                                                (SEQ ID NO: 50)
  5'-GGCCCTACGTACGCGTGGCGATTCCTTATGGTCCAG-3'

DH-1_downstream_SacI (Reverse):
                                                (SEQ ID NO: 51)
  5'-CTGTCCTCTAGTGAGCTCTGTTGAAGTTATCGGTATCG-3'
```

Electro transformation was performed by introducing the prepared vector for deleting Shc gene into a cultured DH-1 strain using the Gene Pulser Xcell™ Electroporation system (Bio-rad). Subsequently, the DH-1 strain was stabilized by culturing in an NMS medium for 16 hours. The culture was plated on an NMS solid medium containing kanamycin and cultured for one week to induce double crossover homologous recombination, and thereby a transformed DH-1 strain (DH-1/SQU) was prepared.

Whether the DH-1/SQU strain is a transformed strain was confirmed using a method similar to that used in Example 5-2 by using the primers shown below.

```
DH-1_ΔShc (Forward)
                                                (SEQ ID NO: 52)
5'-ACGTCTAGATCTGAATTCCATCTCGGCCGGGTCGGCAATAGC-3'

DH-1_ΔShc (Reverse)
                                                (SEQ ID NO: 53)
5'-CTGTCCTCTAGTGAGCTCTGTTGAAGTTATCGGTATCG-3'
```

Example 6-2: Analysis of Squalene Productivity Using Transformed DH-1 Strain DH-1 strain and DH-1/SQU strains were each inoculated into an NMS medium and cultured in the atmosphere containing methane (30% (v/v)) at 30° C. and at a rate of 230 rpm for 16 and 28 hours, respectively. After completion of the culture, each culture was centrifuged to obtain cell bodies.

The obtained cell bodies was suspended in an extraction solvent (chloroform:methanol=1:2, v/v) and extracted while stirring. The reactants were centrifuged to obtain the supernatant and the obtained supernatant was mixed with acetonitrile and heptanol at a 1:1:2 (v/v/v) ratio, stirred vigorously, and the topmost heptane layer was obtained. Nitrogen was added to the obtained heptane layer and the solvent was evaporated to obtain a residue, and thereby an extract containing squalene was obtained.

Then, for quantification analysis of the squalene contained in the extract, the obtained residue was dissolved in the HPLC solvent (heptane:acetonitrile=5:95, v/v), filtered with a 0.2 μm filter, and quantitatively analyzed (FIG. 6). In particular, the synthesized squalene was used as the reference material, acetonitrile was used as the mobile phase, and the velocity of the mobile phase was set to 1.5 mL/min.

FIG. 6 is a graph showing the comparison results of productivity of squalene synthesized in the DH-1 strain and the DH-1/SQU strain cultured for 16 hours and 28 hours, respectively.

As shown in FIG. 6, the transformed DH-1 strain showed relative superiority in squalene productivity compared to the DH-1 strain, and with the progress of culture time, the difference in squalene productivity increased further. Simply, when cultured for 28 hours, the DH-1 strain showed about 1.0 mg/L DCW of squalene productivity while the transformed DH-1 strain showed about 1.41 mg/g DCW of squalene productivity, thus confirming that the DH-1/SQU strain has 1.8-fold increased squalene productivity compared to the DH-1 strain.

It is not known whether or not previously known type 1 or type 2 methanotrophs can biosynthesize squalene from methane.

Unlike such conventional methanotrophs, the DH-1 strain of the present invention was shown to have advantages in that it can significantly improve the efficiency of squalene synthesis via transformation as well as having activity producing squalene from methane.

Example 7: Production of 23-Butanediol Using Transformed Methanotrophs

After amplifying the pAWP89 vector (i.e., an IncP-based vector), each gene encoding α-acetolactate synthase (ALS), α-acetolactate decarboxylase (ALDC), and 2,3-butanediol dehydrogenase (BDH) (SEQ ID NOS: 54, 55, and 56) was amplified using the primers shown below and ligated to the amplified vector, and thereby the expression vector for methanotrophs including the budABC gene (SEQ ID NO: 57) was prepared.

```
pAWP89-Tac/Forward:
                                      (SEQ ID NO: 58)
5'-TAGTTGTCGGGAAGATGCGT-3' pAWP89-Tac/Reverse:
                                      (SEQ ID NO: 59)
5'-AGCTGTTTCCTGTGTGAATA-3'

BudABC-Kleb-Forward:
                                      (SEQ ID NO: 60)
5'-TTCACACAGGAAACAGCTATGAATCATTCTGCTGAATGCACC-3'

BudABC-Kleb-Reverse:
                                      (SEQ ID NO: 61)
5'-GCATCTTCCCGACAACTATTAGTTAAACACCATGCCGCC-3'
```

The expression vector for methanotrophs obtained in Example 1 was transformed into a wild-type methanotroph (*M. alcaliphilum* strain 20Z) by electroporation.

Briefly, after culturing the methanotroph, the above-prepared expression vector was introduced into the methanotroph using the Gene Pulser Xcell™ Electroporation system (Bio-rad). Then, the methanotroph was recovered, transferred into an NMS medium (10 mL) and stabilized by culturing by supplying a methane substrate. The resulting culture was plated on a solid NMS medium containing kanamycin and cultured to prepare a transformed methanotroph.

An attempt was made to examine whether or not 2,3-butanediol can be produced from a methane substrate through the prepared transformed methanotroph. In particular, a wild-type methanotroph (*M. alcaliphilum* strain 20Z) was used as the control strain.

Briefly, a wild-type methanotroph and a transformed methanotroph were each inoculated into an NMS medium. While culturing in the atmosphere containing methane (50% (v/v)) at 30° C. at a rate of 230 rpm in the atmosphere, culture samples (1 mL each) were collected at regular time intervals, centrifuged, and the supernatant was filtered with a 0.2 μm filter. Then, 2,3-butanediol was analyzed by HPLC equipped with an Aminex HPX-87H column (FIGS. 7A to 7C). In particular, for the analysis, 0.005 M $H_2SO_4$ was used as the mobile phase, the flow rate was set to 0.7 mL/min, and the oven temperature was set to 60° C.

FIG. 7A is a graph showing the results comparing 2,3-butanediol production between a wild-type methanotroph and a transformed methanotroph (in which the budABC gene-containing expression vector for methanotrophs was introduced into a wild-type methanotroph (*M. alcaliphilum* strain 20Z)), after culturing the wild-type methanotroph and the transformed methanotroph using methane as a substrate for 96 hours, respectively.

As shown in FIG. 7A, the wild-type methanotroph did not produce 2,3-butanediol, but the transformed methanotroph produced 2,3-butanediol.

FIG. 7B is a graph showing the results confirming the amounts of acetoin and 2,3-butanediol production from methane using a transformed methanotroph, after transforming the budABC gene-containing expression vector for methanotrophs into the wild-type methanotroph (*M. alcaliphilum* strain 20Z).

As shown in FIG. 7B, it was confirmed that the transformed methanotroph produced acetoin (i.e., a precursor of 2,3-butanediol) at the initial stage of growth, and produced 2,3-butanediol based on the same.

FIG. 7C is a graph showing the results confirming the amount of 2,3-butanediol production from methane using a transformed methanotroph and cell growth rate thereof, after transforming the budABC gene-containing expression vector for methanotrophs into the wild-type methanotroph (*M. alcaliphilum* strain 20Z).

As shown in FIG. 7C, it was confirmed that the transformed methanotroph produced 2,3-butanediol during the growth and the maximum production of 2,3-butanediol was 38 mg/mL.

Taken together, it was confirmed that the methanotroph, which was transformed so that ALS, ALDC, and BDH can be expressed, can produce 2,3-butanediol using methane as a substrate.

Example 8: Production of 23-Butanediol Using Transformed *E. coli*

The transformed *E. coli*, which can biosynthesize 2,3-butanediol from ethanol, was prepared by introducing a gene encoding methanol dehydrogenase and a gene encoding formolase (FLS), which is an aldehyde lyase.

Example 8-1: Preparation of Recombinant Vector

First, an mdh gene encoding $NAD^+$-dependent methanol dehydrogenase derived from *Bacillus methanolicus* MGA3 was synthesized by modifying into an optimized sequence (SEQ ID NO: 62) to be expressed in *E. coli*, and the synthesized mdh gene was cloned into the pACYCDuet™-1 vector (Novagen) to obtain the recombinant vector, pMDH.

Second, the gene encoding formolase (FLS) (SEQ ID NO: 63), which is an aldehyde lyase, was synthesized, and the synthesized FLS gene was cloned into the pACYCDuet™-1 vector (Novagen) to obtain the recombinant vector, pFLS.

Third, the synthesized FLS gene was cloned into the pET21 b(+) vector (Novagen) to obtain the recombinant vector, pFLS_2.

Fourth, the synthesized mdh gene and FLS gene were cloned into the pACYCDuet™-1 vector (Novagen) to obtain the recombinant vector, pMDHFLS.

Fifth, a budABC gene encoding 2,3-butanediol dehydrogenase (bdh1), which is an acetoin reductase, was synthesized, and the synthesized budABC gene was cloned into the pAWP89 vector (Addgene) to obtain the recombinant vector, pBUD.

Example 8-2: Preparation of Transformed *E. coli*

The four kinds of recombinant vectors synthesized in Example 8-1 were introduced into (*E. coli* BL21 (DE3)), and thereby each transformed *E. coli* was prepared.

Specifically, a transformed *E. coli* BL21-pMDH was prepared by introducing the recombinant vector pMDH into *E. coli*; a transformed *E. coli* BL21-pFLS was prepared by introducing the recombinant vector pFLS into *E. coli*; a transformed *E. coli* BL21-pMDHFLS was prepared by introducing the recombinant vector pMDHFLS into *E. coli*: a transformed *E. coli* BL21-pMDHFLS2 was prepared by introducing the recombinant vectors pMDH and pFLS_2 together into *E. coli*; and a transformed *E. coli* BL21-pMDHFLSBUD was prepared by introducing the recombinant vectors pMDH, pFLS_2, and pBUD together into *E. coli*.

Each of the prepared transformed *E. coli* strains was cultured in an LB medium (10 mL) overnight, and each overnight culture was inoculated into an LB medium and cultured to an absorbance (OD600) of 0.5 to 0.6. Then, 0.1 mM isopropyl 3-D-1-thiogalactopyranoside (IPTG) was added thereto to induce gene transcription, and the proteins were expressed at 37° C. for 4.5 hours or at 15° C. for 24 hours.

Example 8-3: Production of 2,3-Butanediol Using Transformed *E. coli*

Among the transformed *E. coli* strains prepared in Example 8-2, the BL21-pMDHFLS2 was cultured and two kinds of introduced genes were expressed, and reacted in an LB medium or M9 medium containing ethanol or glucose, and the quantification analysis of acetoin produced as a reaction product was performed (FIG. 8A).

FIG. 8A is a graph showing the results of quantification analysis with regard to the level of acetoin produced from BL21-pMDHFLS2 (i.e., a transformed *E. coli*), in a medium condition where ethanol and glucose are contained alone or together.

As shown in FIG. 8A, it was confirmed that it is possible to produce acetoin in high yield only when the LB medium containing ethanol is used.

Among the transformed *E. coli* strains prepared in Example 8-2, the transformed *E. coli* BL21-pMDHFLS2 and the transformed *E. coli* BL21-pMDHFLSBUD (in which pBUD was added to the transformed *E. coli* BL21-pMDHFLS2) were cultured in a liquid LB medium containing ethanol (1.7% (v/v)) and the reaction products in the culture were analyzed by HPLC (FIG. 8B). In particular, a wild-type *E. coli* was used as the control.

FIG. 8B is a graph showing the results of HPLC analysis with regard to the components, which are contained in the culture product of a transformed *E. coli* capable of expressing MDH and FLS (a recombinant strain producing acetoin) cultured in an ethanol-containing medium, and in the culture product of a transformed *E. coli* capable of expressing MDH, FLS, and bdh1 (a recombinant strain producing 2,3-butanediol), respectively.

As shown in FIG. 8B, it was confirmed that while the transformed *E. coli* capable of expressing MDH and FLS were able to produce only acetoin using ethanol, the transformed *E. coli* capable of expressing FLS and bdh1 were able to produce 2,3-butanediol as well as acetoin, by using ethanol.

As can be seen in the results above, it was confirmed that the transformed *E. coli* capable of expressing methanol dehydrogenase (MDH), formolase (FLS), which is an aldehyde lyase, and 2,3-butanediol dehydrogenase (bdh1) were able to produce 2,3-butanediol from ethanol via the chain reaction of the expressed enzymes.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A method for producing metabolites from a gaseous alkane compound, which comprises culturing a *Methylomonas* sp. DH-1 strain, deposited under Accession Number KCTC18400P, or a transformant thereof under atmospheric conditions.

2. The method of claim 1, wherein the *Methylomonas* sp. DH-1 strain exhibits the following characteristics that:
   (a) a soluble methane monooxygenase (sMMO) gene is not present;
   (b) a gene is expressed which is selected from the group consisting of a particulate methane monooxygenase (pMMO) gene, a PQQ-dependent methanol dehydrogenase (mxaFJGIRSACKLDEK) gene, a PQQ biosynthesis gene cluster (pqqBCDE) gene, a pyruvate decarboxylase (PDC) gene, a glutamyl-tRNA synthase (gltX) gene, an NADPH-dependent glutamyl-tRNA reductase (hemA) gene, a glutamate-1-semialdehyde aminotransferase (hemL) gene, a squalene hopene cyclase (shc) gene, and a combination thereof;
   (c) a pathway is activated which is selected from the group consisting of ribulose monophosphate (RuMP) cycle involved in formaldehyde metabolism, Entner-Doudoroff (ED) pathway, Embden-Meyerhof-Parnas (EMP) pathway, pentose phosphate (PP) pathway, tetrahydromethanopterim ($H_4$MPT) pathway, tetrahydrofolate ($H_4$F) pathway, serine pathway, TCA cycle, C30 carotenoid synthesis pathway, hopanoid biosynthesis pathway, C40 carotenoid synthesis pathway, and a combination thereof; and
   (d) carbon dioxide is absorbed and fixed by a combination of a pyruvate carboxylase gene, a phosphoenolpyruvate carboxylase gene, and a pyruvate decarboxylase (PDC) gene.

3. The method of claim 1, wherein the gaseous alkane compound is a gaseous lower alkane compound.

4. The method of claim 3, wherein the lower alkane compound is an alkane compound having 1 to 6 carbon atoms.

5. The method of claim 1, wherein the content of gaseous alkane compound in the atmosphere is in a range of 10% (v/v) to 80% (v/v).

6. The method of claim 1, wherein the metabolites are selected from the group consisting of lower alcohol, TCA cycle components, squalene, δ-aminolevulinic acid, and a combination thereof.

7. The method of claim 6, wherein the lower alcohol is selected from the group consisting of methanol, ethanol, propanol, butanol, 2,3-butanediol, pentanol, hexanol, and a combination thereof.

8. The method of claim 6, wherein the TCA cycle components are selected from the group consisting of succinic acid, oxaloacetate, citric acid, malic acid, succinyl-CoA, and a combination thereof.

9. The method of claim 1, wherein ethanol is produced from gaseous ethane using the *Methylomonas* sp. DH-1 strain.

10. The method of claim 1, wherein propanol is produced from gaseous propane using the *Methylomonas* sp. DH-1 strain.

11. The method of claim 1, wherein succinic acid is produced from gaseous methane using the *Methylomonas* sp. DH-1 strain.

12. The method of claim 1, wherein δ-aminolevulinic acid is produced from gaseous methane using the *Methylomonas* sp. DH-1 strain.

13. The method of claim 1, wherein squalene is produced from gaseous methane using the *Methylomonas* sp. DH-1 strain.

14. The method of claim 1, wherein the transformant is a strain, in which an acetoin reductase gene is introduced into a *Methylomonas* sp. DH-1 strain and 2,3-butanediol is produced from gaseous ethane using the transformant.

15. The method of claim 1, wherein the transformant is a strain, in which a gene encoding succinic acid dehydrogenase (SDH) is deleted in a *Methylomonas* sp. DH-1 strain and succinic acid is produced from gaseous methane using the transformant.

16. The method of claim 15, wherein the transformant is a strain, in which a gene encoding isocitrate dehydrogenase and a gene encoding malate synthase are further introduced into the transformant and succinic acid is produced from gaseous methane using the transformant.

17. The method of claim 16, wherein the transformant is a strain, in which a gene encoding phosphoacetyl transferase (pta) and a gene encoding acetate kinase (ack) are further deleted in the transformant and succinic acid is produced from gaseous methane using the transformant.

18. The method of claim 1, wherein the transformant is a strain, in which a gene encoding δ-aminolevulinic acid synthase (ALAS) is introduced into a *Methylomonas* sp. DH-1 strain and δ-aminolevulinic acid is produced from gaseous methane using the transformant.

19. The method of claim 1, wherein the transformant is a strain, in which a gene encoding squalene hopene cyclase (Shc) is deleted in a *Methylomonas* sp. DH-1 strain and squalene is produced from gaseous methane using the transformant.

* * * * *

SEQUENCE LISTING

```
<160> NUMBER OF SEQ ID NOS: 63

<210> SEQ ID NO 1
<211> LENGTH: 2950
<212> TYPE: DNA
<213> ORGANISM: Artificial Sequence
<220> FEATURE:
<223> OTHER INFORMATION: recombinant pMMO

<400> SEQUENCE: 1
atggctgcta caactgaatc agttaaggct gatgctgcgg aagcaccgct tttaaatcaa      60
agaaacctat gggcgggcgt tgctctgtac ttggttttct attctttcat tcgttggtac     120
gaaggcgtct acggctggtc agctggtctg gactcatttg ctccagagtt tgaaacatac     180
tggatgaaca tgctgtacat cgagatcgta gccgaagttg tcctgttcgc aggtatcaac     240
ggttacatct ggaaaactcg tgatcgcaaa gtaatgtcaa tcactccacg tgaagaactg     300
cgtcgtcatt tcacacactg gacatggttg gtttgctacg gttgggcaat ctactggggt     360
gcttcttact tcacagagca agacggtact tggcatcaaa ccatcgttcg tgatactgac     420
tttactccaa gtcacatcat cgaattttac ctgtcatacc caatttacat catcactggc     480
acagcttctt tcatgtacgc taaaaccaga ctgcctacct atcaagaagg tctgcatttg     540
atgtatttgg ttgttgttat tggtccgttc atgattctgc caaacgttgg tttgaacgaa     600
tggggtcaca cattctggtt tatggaagag ttgttcgttg ctccattgca ctacggtttc     660
gtattctttg gtttgggctg tctgggtatt ctgggtgtgt tgaataccga agttatggca     720
```

| | |
|---|---|
| attgccaaat tgctgaaaaa agacctggct taatcgctta agtctaaaag taaaatacta | 780 |
| tctcctttct tgccccgtct aggcggggca agataaaggg aaagtaacaa aaaatataat | 840 |
| tttaattctt taggaggtaa gctaatgagc gcatctcaat cagctgtacg ttctcgtgcg | 900 |
| gaagcggtac aagtttcccg tacgtttgac tggatgattc tttttacact gttcacagcg | 960 |
| gttctgggcg gttatcacat tcactatatg ttgactggtg gtgactggga cttctggacc | 1020 |
| gactggaaag atagacgtct gtgggtaacc gtagctccta tcgtttctat tactttccct | 1080 |
| gcggctgttc aagcttgctt gtggtggaga taccgtttgc caatcggcgc aaccatttct | 1140 |
| gttgttgctc tgatgattgg tgagtggatc aaccgttaca tgaacttctg ggttggact | 1200 |
| tacttcccag taaacatttg cttcccatct aaccttctgc caggcgctat cgttcttgat | 1260 |
| gtgatcctga tgttgggtaa cagcatgacc ttgactgctg ttttgggtgg tttggcttac | 1320 |
| ggtttgttgt tctacccagg caactggccg gtaattgctc ctcttcacgt tcctgtagag | 1380 |
| tacaacggca tgatgatgac cctggctgac ttgcaaggtt accactatgt tcgtaccggt | 1440 |
| acacctgagt acatccgtat ggttgagaaa ggtacattaa gaactttcgg taaagacgtt | 1500 |
| gctcctgtat cagcgttctt ctctggattc gtttctatca tcatctactt cttgtggcac | 1560 |
| ttctttggca gatggttcgc tcaaaccgga ttcatcgccg acgacgcatc ctaatctgaa | 1620 |
| gttttgattg aaaatgaaag ctggcgcacc ttaaaagtgc cagcaggtct taattacaag | 1680 |
| attctctagt aatagaggag gaaatatgaa aataataaaa gacaaagttg caaaactgtc | 1740 |
| ctttgtcgca ctgttggttg caatggcaac agcgatgttc tacgctccag cagcatctgc | 1800 |
| tcatggtgaa aagtcacagg ctgcgttcat gcgtatgcgt actattcact ggtttgactt | 1860 |
| gaactggtca aagaagaag tagctgtcaa cgatactatg acaatttccg gtaaattcct | 1920 |
| ggtattcgca ggttggccag aaactgttga taaaccagaa gtttcatttt tgaacgttgg | 1980 |
| tatccctggt ccagtattca ttcgtgctgg ttcttggatc ggcggtcaac tggttccacg | 2040 |
| ttctgttcct ttggaactgg gcgaagttta cgagtttaaa gtactgttga agctcgtcg | 2100 |
| tcctggcgac tggcacgttc actctatgat gaacgtacaa ggcggtggtc caatcatcgg | 2160 |
| tcctggtaaa tgggtaactg taactggttc tatgagcgag ttcgtaaacc ctgttaccac | 2220 |
| tttgactggt caaaccatca acttggaaaa ctacgctctg ataacgtttt acttctggca | 2280 |
| cgctgtatgg ttcgcaatcg cgtttgcttg gttgatcttt tgggtcaaac gtccgatttt | 2340 |
| cgttccacgt cacatcgctg ttagcacagg taaagcagac tctttgatct cagctggtga | 2400 |
| caaaaaagtc ggtatgttgt tcggcgttgg taccatggtt atcgtagcgg cttctatggc | 2460 |
| gtctactaac gaaaaatacc ctgttactac tccgctgcaa gctggtttgt tgcgtggtat | 2520 |
| gaaaacttat caaatgcctg aagctactgt ttcagttaaa gttgatgacg ctacataccg | 2580 |
| tgtaccaggt cgtgcaatgc aaatgacctt gacagtaaca aacaacggcg attctgctgt | 2640 |
| ccgtttgggt gaattcaaca cagctggcgt tcgcttcttg gatcctgctg ttcacgaaga | 2700 |
| tgacaccaac tatcctgacg acttgttggc tgaagaaggt ctgactgtta gcgataacag | 2760 |
| cccgctggct ccaggtgaaa cccgcactat cgaagttacc gcttctgatg ctgcttggga | 2820 |
| agtttaccgt ctggctgact tgatctatga cccagacagc cgtttcgctg gcttgttgtt | 2880 |
| cttctgggat gcaaacggca accgtcaatt ggtaactgtt gacgctccgc tgatcccgac | 2940 |
| tttcatctaa | 2950 |

<210> SEQ ID NO 2
<211> LENGTH: 546

```
<212> TYPE: PRT
<213> ORGANISM: Artificial Sequence
<220> FEATURE:
<223> OTHER INFORMATION: recombinant pyruvate decarboxylase

<400> SEQUENCE: 2
```

Met Ser Ser Gln Ser Ala Glu Ser Ile Gly Gln Tyr Leu Leu Glu Arg
1               5                   10                  15

Leu Tyr Ala Leu Gly Val Arg Asp Ile Phe Gly Val Pro Gly Asp Tyr
            20                  25                  30

Ile Leu Gly Phe Tyr Asp Gln Met Val His Ser Pro Ile Arg His Ile
        35                  40                  45

Gly Thr Thr Arg Glu Asp Thr Ala Ala Phe Ala Ala Asp Gly Tyr Ala
    50                  55                  60

Arg Cys Ser Gly Leu Gly Ala Val Ala Val Thr Tyr Gly Val Gly Ala
65                  70                  75                  80

Leu Asn Thr Val Asn Ala Val Ala Gly Ala His Ala Glu Ser Ser Pro
                85                  90                  95

Val Val Val Ile Ser Gly Ala Pro Gly Val Glu Glu Gln Arg Asn Asp
                100                 105                 110

Pro Leu Leu His His Arg Phe Gly Pro Phe Thr Phe Gln Arg Glu Ile
            115                 120                 125

Phe Glu Arg Ile Thr Cys Ala Ser Val Val Leu Asn Asp Pro Val Ile
        130                 135                 140

Ala Cys Arg Gln Ile Asp Gln Ala Leu Ala Ala Ala Arg His Tyr Ser
145                 150                 155                 160

Lys Pro Val Tyr Ile Glu Ile Pro Arg Asp Arg Val Arg Val Ala Gly
                165                 170                 175

Tyr Pro Ile Pro Glu Pro Ala Gln Glu Ala Phe Gly Ser Asp Glu Thr
            180                 185                 190

Ala Leu Ala Glu Ala Val Ala Glu Thr Met Glu Leu Gly Glu Lys Ser
        195                 200                 205

Arg Ser Pro Ile Ile Val Ala Gly Val Glu Ile His Arg Arg Gly Leu
    210                 215                 220

Gln Gly Val Leu Val Asp Leu Val Asn Arg Ser Gly Leu Pro Val Ala
225                 230                 235                 240

Ala Thr Leu Thr Gly Lys Ser Val Ile Ala Glu Arg His Pro Ala Tyr
                245                 250                 255

Leu Gly Ile Tyr Glu Gly Ala Met Ser Ala Glu Tyr Thr Arg Tyr Leu
            260                 265                 270

Val Glu Gln Ala Asp Leu Leu Leu Met Leu Gly Val Thr Leu Asn Asp
        275                 280                 285

Val Asp Thr Gly Ile Tyr Thr Ala Lys Leu Asp Pro Gln His Met Val
    290                 295                 300

Arg Ala Ala Gln Asp Glu Val Val Ile Ser Ser His Arg Tyr Pro Arg
305                 310                 315                 320

Val Leu Leu Lys Asp Phe Leu His Ala Leu Ala Lys Ser Val Pro Val
                325                 330                 335

Arg Pro Glu Lys Phe Val Ala Pro Ala Ala Val Thr Ala Pro Asp
            340                 345                 350

Phe Pro Ala Pro Asp Arg Ala Ile Thr Thr Ser Arg Leu Val Gly Arg
        355                 360                 365

Leu Asn Gln Ala Leu Gly Pro Glu Phe Ile Val Val Cys Asp Val Gly
    370                 375                 380

```
Asp Cys Leu Phe Ala Thr Ile Asp Leu Gln Val His Glu Gln Ser Glu
385                 390                 395                 400

Phe Leu Ser Ser Ala Phe Tyr Thr Ser Met Gly Phe Ala Val Pro Ala
            405                 410                 415

Ala Leu Gly Ala Gln Ile Ala Arg Arg Asp Arg Arg Ala Leu Val Leu
        420                 425                 430

Val Gly Asp Gly Ala Phe Gln Met Thr Gly Thr Glu Leu Ala Thr Phe
    435                 440                 445

Ala Arg Leu Gly Leu Asp Pro Ile Val Val Val Phe Asn Asn Arg Gly
    450                 455                 460

Tyr Ser Thr Glu Arg Phe Ile Leu Glu Gly Pro Phe Asn Asp Ile Gly
465                 470                 475                 480

Asp Trp Arg Phe Asp Arg Leu Gly Glu Val Phe Gly Pro Leu Gln Gly
            485                 490                 495

Tyr Ala Ala Ser Thr Glu Glu Ala Phe Glu Ala Ala Leu Val Ala Ala
                500                 505                 510

Leu Glu Asn Arg Ser Ser Pro Ser Ile Ile Asn Val Arg Leu Asp Pro
            515                 520                 525

Ala Asp Ala Ser Ala Ala Met Gln Arg Leu Ala Ala His Leu His Ser
            530                 535                 540

Arg Val
545

<210> SEQ ID NO 3
<211> LENGTH: 256
<212> TYPE: PRT
<213> ORGANISM: Artificial Sequence
<220> FEATURE:
<223> OTHER INFORMATION: recombinant acetoin reductase

<400> SEQUENCE: 3

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly Arg Ala Met Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190
```

```
Ile Asp Arg Gln Val Ser Glu Ala Ala Gly Lys Pro Leu Gly Tyr Gly
            195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255

<210> SEQ ID NO 4
<211> LENGTH: 465
<212> TYPE: PRT
<213> ORGANISM: Artificial Sequence
<220> FEATURE:
<223> OTHER INFORMATION: recombinant gltX

<400> SEQUENCE: 4

Met Ser Ile Arg Thr Arg Phe Ala Pro Ser Pro Thr Gly Tyr Leu His
1               5                   10                  15

Val Gly Gly Ala Arg Thr Ala Leu Phe Ser Trp Leu Tyr Ala Arg Lys
                20                  25                  30

His Gly Gly Arg Phe Ile Leu Arg Ile Glu Asp Thr Asp Leu Glu Arg
            35                  40                  45

Ser Ser Gln Glu Ser Val Asn Ala Ile Leu Glu Gly Met Thr Trp Leu
    50                  55                  60

Gly Leu Glu Tyr Asp Glu Gly Pro Phe Tyr Gln Thr Gln Arg Phe Asp
65                  70                  75                  80

Arg Tyr Lys Glu Val Ile Gln Gln Leu Leu Asp Gln Gly Asp Ala Tyr
                85                  90                  95

Tyr Cys Tyr Cys Ser Arg Glu Glu Leu Asp Ala Leu Arg Glu Gln Gln
            100                 105                 110

Met Ala Asn Lys Glu Lys Pro Arg Tyr Asn Gly Lys Cys Arg His Gly
    115                 120                 125

Val Ser Asn Pro Ser Gly Glu Pro Val Val Arg Phe Lys Asn Leu Glu
130                 135                 140

Ser Gly Glu Val Val Ile Asp Asp Leu Val Lys Gly Arg Ile Val Val
145                 150                 155                 160

Ala Asn Lys Glu Leu Asp Asp Leu Ile Ile Ala Arg Ser Asp Gly Thr
                165                 170                 175

Pro Thr Tyr Asn Leu Thr Val Val Asp Asp Met Asp Met Gly Val
            180                 185                 190

Thr His Val Ile Arg Gly Asp Asp His Val Asn Asn Thr Pro Arg Gln
    195                 200                 205

Ile Asn Ile Leu Gln Ala Leu Gly Ala Pro Leu Pro Ile Tyr Ala His
210                 215                 220

Val Pro Met Ile Leu Gly Pro Asp Gly Ala Arg Leu Ser Lys Arg His
225                 230                 235                 240

Gly Ala Val Ser Val Met Gln Tyr Arg Asn Asp Gly Tyr Leu Pro Glu
                245                 250                 255

Ala Leu Leu Asn Tyr Leu Val Arg Leu Gly Trp Ser His Gly Asp Gln
            260                 265                 270

Glu Leu Phe Ser Ile Glu Gln Met Ile Glu Leu Phe Glu Leu Glu Lys
    275                 280                 285

Val Asn Val Ser Ala Ser Thr Phe Asn Thr Asp Lys Leu Ile Trp Leu
290                 295                 300
```

-continued

Asn His Gln Tyr Ile Met Asn Ser Asp Pro Ala His Val Ala Arg His
305                 310                 315                 320

Leu Ala Trp His Met Gly Glu Arg Gly Ile Asp Pro Ala Thr Gly Pro
            325                 330                 335

Ala Leu Ser Glu Val Val Lys Ala Gln Arg Glu Arg Cys Lys Thr Leu
        340                 345                 350

Val Asp Met Ala Asn Asp Ser Val Tyr Phe Tyr Arg Asp Phe Ala Glu
    355                 360                 365

Tyr Asp Asp Lys Ala Val Lys Lys Asn Phe Lys Ala Gly Val Asp Asp
    370                 375                 380

Val Leu Gln His Leu Arg Asp Gln Phe Gly Ala Leu Ala Asp Trp Glu
385                 390                 395                 400

Ala Asp Ala Leu His Gln Val Val Leu Asp Ser Ala Glu Arg Leu Gln
            405                 410                 415

Leu Asn Leu Gly Lys Val Ala Gln Pro Leu Arg Val Ala Val Cys Gly
            420                 425                 430

Gly Ser Val Ser Pro Ala Ile Asp Val Thr Leu Lys Leu Leu Gly Arg
        435                 440                 445

Glu Lys Thr Leu Asn Arg Leu Asp Arg Ala Ile Glu Phe Ile Lys Lys
    450                 455                 460

Leu
465

<210> SEQ ID NO 5
<211> LENGTH: 416
<212> TYPE: PRT
<213> ORGANISM: Artificial Sequence
<220> FEATURE:
<223> OTHER INFORMATION: recombinant hemA

<400> SEQUENCE: 5

Met Thr Leu Leu Ala Val Gly Ile Asn Tyr Asn Thr Ala Pro Val Ala
1               5                   10                  15

Val Arg Glu Arg Leu Ala Phe Pro Ser Glu Ala Leu Glu Ser Thr Leu
            20                  25                  30

Lys Asn Leu Trp Ser Ile Arg Glu Ile Ser Glu Ala Ala Ile Leu Ser
        35                  40                  45

Thr Cys Asn Arg Thr Glu Phe Tyr Cys Gln Ala Asp Ser Asp Asp Gln
    50                  55                  60

Ser Ser Leu Val Glu Trp Ile Ala Asp Thr Lys Arg Ile Lys Pro Ala
65                  70                  75                  80

Glu Phe Thr Pro Tyr Leu Tyr Ser Tyr Lys Asp Ser Gln Ser Ile Arg
                85                  90                  95

His Met Phe Arg Val Ala Cys Gly Leu Asp Ser Met Ile Leu Gly Glu
            100                 105                 110

Pro Gln Ile Leu Gly Gln Met Lys Thr Ala Tyr His Ala Ala Ser Gln
        115                 120                 125

Ala Gly Thr Leu Gly Arg Asn Leu Ser Lys Leu Phe Gln His Thr Phe
    130                 135                 140

Ser Ala Ala Lys Lys Val Arg Thr Asp Thr Ala Ile Gly Ser Ser Pro
145                 150                 155                 160

Val Ser Val Ala Phe Ala Ala Val Gln Leu Ala Gln Gln Ile Phe Asp
                165                 170                 175

Lys Leu Ser Asp Gln Thr Ala Leu Leu Ile Gly Ala Gly Glu Thr Ile
            180                 185                 190

```
Glu Leu Thr Ala Arg His Leu Phe Gln His Gly Ile Gly Arg Ile Ile
            195                 200                 205

Ile Ala Asn Arg Thr Tyr Asp Lys Ala His Ala Leu Ala Ala Gln Phe
    210                 215                 220

Asn Gly Tyr Ala Ile Ser Leu Ala Glu Leu Pro Asn His Leu Ala Glu
225                 230                 235                 240

Ala Asp Ile Val Val Ser Ser Thr Ala Ser Gln Leu Pro Ile Leu Gly
                245                 250                 255

Lys Gly Arg Val Glu Ser Ala Ile Lys Ile Arg Lys His Lys Pro Met
                260                 265                 270

Phe Met Val Asp Leu Ala Val Pro Arg Asp Ile Glu Ala Glu Val Gly
            275                 280                 285

His Leu Arg Asp Val Tyr Leu Tyr Thr Val Asp Asp Leu Gln His Thr
            290                 295                 300

Val Asn Gln Asn Met Asp Ser Arg Arg Ala Ala Glu Gln Ala Glu
305                 310                 315                 320

Glu Ile Ile Asp Thr Gln Val Glu His Phe Leu Ala Trp Leu Arg Ser
                325                 330                 335

Gln Gly Ala Gln Glu Thr Ile Arg Asp Tyr Arg Ala Gln Ala Glu Gln
                340                 345                 350

Thr Arg Asp Glu Ala Leu Gln Arg Ala Leu Gln Leu Asn Ser Gly
            355                 360                 365

Ala Ser Ala Glu Asp Val Leu Gln Arg Leu Ala His Thr Leu Thr Asn
    370                 375                 380

Lys Leu Ile His Thr Pro Cys Ala Gln Leu Arg Asp Ala Gly Ala Asn
385                 390                 395                 400

Glu Arg His Asp Leu Ile Ala Ala Ser Arg Glu Ile Phe Lys Leu Arg
                405                 410                 415

<210> SEQ ID NO 6
<211> LENGTH: 429
<212> TYPE: PRT
<213> ORGANISM: Artificial Sequence
<220> FEATURE:
<223> OTHER INFORMATION: recombinant hemL

<400> SEQUENCE: 6

Met Ser Glu Arg Tyr Arg Asn Ser Glu Thr Leu Leu Glu Arg Ala Leu
1               5                   10                  15

Lys Thr Val Pro Leu Gly Ser Gln Thr Phe Ser Lys Ser Lys Thr Gln
                20                  25                  30

Tyr Pro His Gly Val Ser Pro Tyr Phe Ile Gln Arg Gly Arg Gly Ser
            35                  40                  45

His Val Trp Asp Val Asp Gly Asn Glu Tyr Val Asp Phe Ile Asn Gly
    50                  55                  60

Leu Cys Ala Val Thr Leu Gly Tyr Asn Asp Pro Asp Val Thr Glu Ala
65                  70                  75                  80

Val Lys Ala Gln Leu Glu Asp Gly Val Ile Phe Ser Leu Pro His Pro
                85                  90                  95

Ile Glu Met Gln Val Ala Glu Lys Ile Cys Glu Leu Val Pro Cys Ala
            100                 105                 110

Glu Lys Val Arg Phe Gly Lys Asn Gly Ser Asp Ala Thr Ala Gly Ala
        115                 120                 125

Ile Arg Leu Ala Arg Ala His Thr Gly Arg Asp His Val Ala Val Cys
    130                 135                 140
```

```
Gly Tyr His Gly Trp Gln Asp Trp Tyr Ile Gly Ser Thr Leu Arg Asn
145                 150                 155                 160

Arg Gly Val Pro Gln Ala Thr Arg Asp Leu Thr His Thr Phe Ala Tyr
            165                 170                 175

Asn Asp Ile Ala Ser Leu Asp Ser Leu Phe Lys Gln Trp Pro Asp Gln
        180                 185                 190

Ile Ala Ala Val Ile Leu Glu Pro Met Asn Val Val Glu Pro Gln Asp
    195                 200                 205

Gly Phe Leu Glu Asn Val Lys Ala Leu Thr His Lys His Gly Ala Val
210                 215                 220

Leu Ile Phe Asp Glu Thr Ile Thr Gly Phe Arg Tyr Ala Asn Gly Gly
225                 230                 235                 240

Ala Gln Glu Tyr Phe Gly Val Thr Pro Asp Leu Ala Thr Phe Gly Lys
            245                 250                 255

Gly Leu Ala Asn Gly Tyr Pro Val Ser Ala Val Ala Gly Arg Ala Asp
        260                 265                 270

Leu Met Gln Leu Met Glu Glu Val Phe Phe Ser Phe Thr Phe Gly Gly
    275                 280                 285

Glu Thr Leu Ser Leu Ala Ala Ala Leu Ala Thr Met Gln Lys Leu Gln
290                 295                 300

Arg Glu Pro Val Val Ala Thr Met His Arg Gln Gly Glu Lys Ile Ile
305                 310                 315                 320

Gln Arg Leu Asn Ala Val Ile Ser Glu Gln Gly Ala Glu Gln Phe Leu
            325                 330                 335

Ser Val Ser Gly His Pro Ala Trp Ser Phe Leu Leu Ile Lys Asp Ala
        340                 345                 350

Glu Pro Tyr Thr Ser Trp Gln Leu Lys Thr Leu Phe Met Gln Glu Met
    355                 360                 365

Leu Glu Arg Gly Ile Leu Ala Phe Gly Ser His Asn Met Ser Tyr Ser
370                 375                 380

His Arg Asp Asp Asp Leu Asp Gln Leu Phe Ala Ala Tyr Asp Ala Val
385                 390                 395                 400

Ile Pro Leu Leu Val Ala Ala Val Lys Glu Arg Ser Leu Pro Lys Met
            405                 410                 415

Leu Arg Cys Gln Ala Leu Glu Pro Leu Phe Lys Val Arg
        420                 425

<210> SEQ ID NO 7
<211> LENGTH: 1284
<212> TYPE: DNA
<213> ORGANISM: Artificial Sequence
<220> FEATURE:
<223> OTHER INFORMATION: recombinant ALA synthase

<400> SEQUENCE: 7
atggattacc ggcgcttttt cgagacggcg atcacacgtc tccaggacga gcgccgttac      60
cgagtcttcg cccatctcga acgctgcgtc gaatgcttcc gcgcgcgcgct ctggcaccgg    120 gacgacggca cgacgcagga tgtgacgatc tggtgctcca atgattatct cggcatgggc    180
cagcaccccg aggtgatcgc cgctatggtc gacaccgccg cgcgcgtcgg cgccggctcg    240
ggcggcacgc gcaacatctc cggcaccagc catgcgatcg tcgagctgga gagcgagctc    300
gccgacctgc acggcaagga ggcggcgctc gtcttcacct cgggatggat ttccaatctc    360
gcggcgatct ccacgatcgc cgatcttctg cccgactgtc tcatcctctc cgacgcctcc    420
aatcacaatt cgatgatcga gggcgtcaag cgctcgcgcg ccgagcgcaa gatcttccgc    480
```

```
cacaacgacc tcggccatct cgaggagctg ctcgccgcgg ccggcgcgcg gcccaagctc    540
atcgtcttcg agagcctcta ttcgatgaac ggcaatatcg cgccggtcgc cgagatcgcc    600
gcgctcgccg agcgttatgg cgcgatgacc tatatcgacg aggttcatgc ggtcggcatg    660 tatgcgcgc gcggcggcgg cgtttgcgag caggccggcg tgatggaccg tatcgatgtg     720
atcgagggca cgctggccaa gggcttcggc acgctcggcg gctatatcgc cggcgatcgc    780
gtcatcatcg acgcgatccg cagctatgcg gcgtccttca tcttcaccac agctctgccg    840
ccggcggtcg ccgcggcggc gaccgccgct gtgcgcctct tgaagacgcg ccccgatctg    900
cgcgccgcgc atcagcgcgc cacccatatc accaagcacg cgctcggcgc cgcgggcctg    960
ccggtgctgg agaacggctc gcatatcgtg ccggtgatgg tgcgcgaggc ggagctgtgc   1020
aaggccgcga gcgacatgct gctcgagcgg cacggcatct atattcagcc gatcaattat   1080
ccgacggtcg cacgcgggac ggagcgtctg cgcatcacgc cgacgccctg ccatacgggc   1140
gagcatatcg tcacgctggt cgaagcgatg gtcgatgtct ggaacacgct cggcatcgcc   1200
ttcgtcgagc cgccgcagca tctccacgtc gatcccgaga gccgcgagcg ctgtacctat   1260
cccgagatca agctcgccgc gcaa                                          1284

<210> SEQ ID NO 8
<211> LENGTH: 428
<212> TYPE: PRT
<213> ORGANISM: Artificial Sequence
<220> FEATURE:
<223> OTHER INFORMATION: recombinant ALA synthase

<400> SEQUENCE: 8

Met Asp Tyr Arg Arg Phe Phe Glu Thr Ala Ile Thr Arg Leu Gln Asp
1               5                   10                  15

Glu Arg Arg Tyr Arg Val Phe Ala His Leu Glu Arg Cys Val Glu Cys
                20                  25                  30

Phe Pro Arg Ala Leu Trp His Arg Asp Asp Gly Thr Thr Gln Asp Val
            35                  40                  45

Thr Ile Trp Cys Ser Asn Asp Tyr Leu Gly Met Gly Gln His Pro Glu
    50                  55                  60

Val Ile Ala Ala Met Val Asp Thr Ala Ala Arg Val Gly Ala Gly Ser
65                  70                  75                  80

Gly Gly Thr Arg Asn Ile Ser Gly Thr Ser His Ala Ile Val Glu Leu
                85                  90                  95

Glu Ser Glu Leu Ala Asp Leu His Gly Lys Glu Ala Ala Leu Val Phe
                100                 105                 110

Thr Ser Gly Trp Ile Ser Asn Leu Ala Ala Ile Ser Thr Ile Ala Asp
            115                 120                 125

Leu Leu Pro Asp Cys Leu Ile Leu Ser Asp Ala Ser Asn His Asn Ser
    130                 135                 140

Met Ile Glu Gly Val Lys Arg Ser Arg Ala Glu Arg Lys Ile Phe Arg
145                 150                 155                 160

His Asn Asp Leu Gly His Leu Glu Glu Leu Leu Ala Ala Ala Gly Ala
                165                 170                 175

Arg Pro Lys Leu Ile Val Phe Glu Ser Leu Tyr Ser Met Asn Gly Asn
            180                 185                 190

Ile Ala Pro Val Ala Glu Ile Ala Ala Leu Ala Glu Arg Tyr Gly Ala
        195                 200                 205

Met Thr Tyr Ile Asp Glu Val His Ala Val Gly Met Tyr Gly Ala Arg
```

```
                210                 215                 220
Gly Gly Gly Val Cys Glu Gln Ala Gly Val Met Asp Arg Ile Asp Val
225                 230                 235                 240

Ile Glu Gly Thr Leu Ala Lys Gly Phe Gly Thr Leu Gly Gly Tyr Ile
                245                 250                 255

Ala Gly Asp Arg Val Ile Ile Asp Ala Ile Arg Ser Tyr Ala Ala Ser
                260                 265                 270

Phe Ile Phe Thr Thr Ala Leu Pro Pro Ala Val Ala Ala Ala Ala Thr
                275                 280                 285

Ala Ala Val Arg Leu Leu Lys Thr Arg Pro Asp Leu Arg Ala Ala His
                290                 295                 300

Gln Arg Ala Thr His Ile Thr Lys His Ala Leu Gly Ala Ala Gly Leu
305                 310                 315                 320

Pro Val Leu Glu Asn Gly Ser His Ile Val Pro Val Met Val Arg Glu
                325                 330                 335

Ala Glu Leu Cys Lys Ala Ala Ser Asp Met Leu Leu Glu Arg His Gly
                340                 345                 350

Ile Tyr Ile Gln Pro Ile Asn Tyr Pro Thr Val Ala Arg Gly Thr Glu
                355                 360                 365

Arg Leu Arg Ile Thr Pro Thr Pro Cys His Thr Gly Glu His Ile Val
                370                 375                 380

Thr Leu Val Glu Ala Met Val Asp Val Trp Asn Thr Leu Gly Ile Ala
385                 390                 395                 400

Phe Val Glu Pro Pro Gln His Leu His Val Asp Pro Glu Ser Arg Glu
                405                 410                 415

Arg Cys Thr Tyr Pro Glu Ile Lys Leu Ala Ala Gln
                420                 425

<210> SEQ ID NO 9
<211> LENGTH: 652
<212> TYPE: PRT
<213> ORGANISM: Artificial Sequence
<220> FEATURE:
<223> OTHER INFORMATION: recombinant squalene hopene cyclase

<400> SEQUENCE: 9

Met Phe Thr Glu Ala Pro Val Glu Thr Ser Asn His Asp Phe Ser His
1               5                   10                  15

His Ser Ser Ala Ala Ile Ser Pro Gly Lys Ile Gln Ala Ala Ile
                20                  25                  30

Asp Arg Ala Gln Ala Lys Leu Leu Ser Leu Gln His Pro Ala Gly Tyr
                35                  40                  45

Trp Val Phe Glu Leu Glu Ala Asp Cys Thr Ile Pro Ser Glu Tyr Ile
                50                  55                  60

Met Met Met His Tyr Leu Asp Asp Ile Asn Glu Glu Leu Gln Ala Lys
65              70                  75                  80

Ile Ala Val Tyr Leu Arg Ser Arg Gln Ser Glu Asp Gly Ser Tyr Pro
                85                  90                  95

Leu Phe Thr Gly Gly Pro Gly Asp Ile Ser Gly Ser Val Lys Ala Tyr
                100                 105                 110

Tyr Ala Leu Lys Met Ala Gly Asp Ala Val Asp Ala Pro His Met Lys
                115                 120                 125

Lys Leu Arg Asp Trp Ile Leu Ser Gln Gly Gly Ala Ala Arg Ala Asn
                130                 135                 140

Val Phe Thr Arg Ile Ala Leu Ala Ile Phe Asp Gln Leu Pro Trp Arg
```

```
            145                 150                 155                 160
        Gly Val Pro Tyr Ile Pro Val Glu Ile Met Leu Leu Pro Lys Trp Phe
                            165                 170                 175
        Pro Phe His Leu Asp Lys Val Ser Tyr Trp Ser Arg Thr Val Met Val
                            180                 185                 190
        Pro Leu Phe Ile Leu Cys Thr Leu Lys Ala Lys Ala Lys Asn Pro His
                            195                 200                 205
        Asn Val Asp Ile Leu Glu Leu Phe Val Val His Pro Asp Glu Lys
            210                 215                 220
        His Tyr Phe Pro Glu Arg Thr Phe Leu Asn Lys Cys Phe Leu Ala Leu
        225                 230                 235                 240
        Asp Lys Leu Gly Arg Val Ala Glu Pro Leu Ile Pro Lys Ser Met Arg
                            245                 250                 255
        Lys Arg Ala Ile Asp Lys Ala Val Ser Trp Phe Thr Glu Arg Leu Asn
                            260                 265                 270
        Gly Glu Asp Gly Leu Gly Gly Ile Phe Pro Ala Met Val Asn Ala Tyr
                            275                 280                 285
        Gln Ala Met Leu Leu Leu Gly Phe Pro Glu Asp His Pro Asn Val Val
                            290                 295                 300
        Ile Ser Arg Lys Ala Ile Asp Lys Leu Leu Val Val Lys Asp Asp Tyr
        305                 310                 315                 320
        Ala Tyr Cys Gln Pro Cys Leu Ser Pro Val Trp Asp Thr Ala Leu Ala
                            325                 330                 335
        Ser Met Ala Leu Ile Glu Ala Asp Lys Arg Gly Asn Thr Pro Gln Leu
                            340                 345                 350
        Ala Lys Ala Asn Asp Trp Leu Lys Ser Val Gln Leu Ser Asp Glu Pro
                            355                 360                 365
        Gly Asp Trp Arg Val Ser Lys Pro Asp Leu Ala Gly Gly Trp Ala
                            370                 375                 380
        Phe Gln Phe Ala Asn Pro His Tyr Pro Asp Val Asp Thr Ala Ile
        385                 390                 395                 400
        Val Gly Phe Ala Met Ala Glu Ser Glu Gln Asp Gly Leu Asp Glu Ser
                            405                 410                 415
        Ile His Arg Ala Thr Arg Trp Ile Val Gly Met Gln Ser Lys Asn Gly
                            420                 425                 430
        Gly Tyr Gly Ala Phe Asp Val Asp Asn Thr Tyr Tyr Leu Asn Glu
                            435                 440                 445
        Ile Pro Phe Ala Asp His Gly Ala Leu Leu Asp Pro Pro Thr Val Asp
            450                 455                 460
        Val Ser Ala Arg Cys Ala Met Leu Met Ala Arg Val Ala Lys Gly His
        465                 470                 475                 480
        Asp Glu Tyr Arg Pro Ala Leu Gln Arg Thr Ile Asp Tyr Ile Arg Ser
                            485                 490                 495
        Glu Gln Glu Ala Asp Gly Ser Trp Phe Gly Arg Trp Gly Thr Asn Phe
                            500                 505                 510
        Ile Tyr Gly Thr Trp Ser Ala Leu Leu Gly Leu Glu Gln Thr Asp Leu
                            515                 520                 525
        Pro Lys Thr Asp Pro Met Tyr Val Lys Ala Ala Trp Leu Lys Ser
                            530                 535                 540
        Val Gln Arg Glu Asp Gly Gly Trp Gly Glu Asp Asn Leu Ser Tyr His
        545                 550                 555                 560
        Asp Asp Val Lys Tyr Arg Gly Arg Tyr His Phe Ser Thr Ala Phe Gln
                            565                 570                 575
```

Thr Ala Trp Ala Ile Leu Gly Leu Ile Ala Ala Gly Glu Val His Ser
            580                 585                 590

Lys Glu Val Lys Ala Gly Ile Glu Phe Leu Leu Arg Ser Gln Gln Ala
        595                 600                 605

Asp Gly Val Trp Asn Asp Pro Cys Phe Thr Ala Pro Gly Phe Pro Arg
    610                 615                 620

Val Phe Tyr Leu Lys Tyr His Gly Tyr Asp Lys Phe Phe Pro Leu Trp
625                 630                 635                 640

Ala Leu Ala Arg Tyr Arg Asn Glu Leu Ser Lys His
                645                 650

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tagttgtcgg gaagatgcgt                                           20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
agctgtttcc tgtgtgaata                                           20

<210> SEQ ID NO 12
<211> LENGTH: 42
<212> TYPE: DNA
<213> ORGANISM: Artificial Sequence
<220> FEATURE:
<223> OTHER INFORMATION: primer

<400> SEQUENCE: 12
ttcacacagg aaacagctat gaatcattct gctgaatgca cc                  42

<210> SEQ ID NO 13
<211> LENGTH: 39
<212> TYPE: DNA
<213> ORGANISM: Artificial Sequence
<220> FEATURE:
<223> OTHER INFORMATION: primer

<400> SEQUENCE: 13
gcatcttccc gacaactatt agttaaacac catgccgcc                      39

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14
aggaaagaaa aatgaaaaaa gtcgcacttg t                              31

<210> SEQ ID NO 15
<211> LENGTH: 32

```
<212> TYPE: DNA
<213> ORGANISM: Artificial Sequence
<220> FEATURE:
<223> OTHER INFORMATION: primer

<400> SEQUENCE: 15
tattgtgatg acccacacat tatacgagcc ga                                    32

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
aattggtacc caaaattcgc agaatatcct                                       30

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
cggtaatacg ggcggtttgc ctggcgctgg                                       30

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
gttaaccggt gtggcaaatt acattttcaa                                       30

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
tagtgagctc tctggctgga ggaattccat                                       30

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20
cggtaatacg ggcggtttgc ctggcgctgg                                       30

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
```
gatgcgtgat atggatgcat atggcggccg                                    30

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
gcaaaccgcc cgtattaccg cctttgagtg                                    30

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23
atgcatccat atcacgcatc ttcccgacaa                                    30

<210> SEQ ID NO 24
<211> LENGTH: 38
<212> TYPE: DNA
<213> ORGANISM: Artificial Sequence
<220> FEATURE:
<223> OTHER INFORMATION: primer

<400> SEQUENCE: 24
acctgacgtc tagatctggt tccgcttgat gggctttg                           38

<210> SEQ ID NO 25
<211> LENGTH: 38
<212> TYPE: DNA
<213> ORGANISM: Artificial Sequence
<220> FEATURE:
<223> OTHER INFORMATION: primer

<400> SEQUENCE: 25
gtaccaattg tacagctggc ggtaaacctg caaatggg                           38

<210> SEQ ID NO 26
<211> LENGTH: 38
<212> TYPE: DNA
<213> ORGANISM: Artificial Sequence
<220> FEATURE:
<223> OTHER INFORMATION: primer

<400> SEQUENCE: 26
cgtgttaacc ggtgagctat cagcgactac caaggcac                           38

<210> SEQ ID NO 27
<211> LENGTH: 38
<212> TYPE: DNA
<213> ORGANISM: Artificial Sequence
<220> FEATURE:
<223> OTHER INFORMATION: primer

<400> SEQUENCE: 27
tggatcctct agtgagctgt tgcagacaga taagcgcg                           38

<210> SEQ ID NO 28
<211> LENGTH: 39
<212> TYPE: DNA
<213> ORGANISM: Artificial Sequence

```
<220> FEATURE:
<223> OTHER INFORMATION: primer

<400> SEQUENCE: 28
cagctgtaca attggtacag gcaatacttc ctctttcgc                              39

<210> SEQ ID NO 29
<211> LENGTH: 42
<212> TYPE: DNA
<213> ORGANISM: Artificial Sequence
<220> FEATURE:
<223> OTHER INFORMATION: primer

<400> SEQUENCE: 29
catatgcatc catggtactt agaactgcga ttcttcagtg ga                          42

<210> SEQ ID NO 30
<211> LENGTH: 38
<212> TYPE: DNA
<213> ORGANISM: Artificial Sequence
<220> FEATURE:
<223> OTHER INFORMATION: primer

<400> SEQUENCE: 30
cgtgttaacc ggtgagctat gtcttgggca aaacaggc                               38

<210> SEQ ID NO 31
<211> LENGTH: 38
<212> TYPE: DNA
<213> ORGANISM: Artificial Sequence
<220> FEATURE:
<223> OTHER INFORMATION: primer

<400> SEQUENCE: 31
tggatcctct agtgagctaa aactcgtcgg tggtgttg                               38

<210> SEQ ID NO 32
<211> LENGTH: 38
<212> TYPE: DNA
<213> ORGANISM: Artificial Sequence
<220> FEATURE:
<223> OTHER INFORMATION: primer

<400> SEQUENCE: 32
acctgacgtc tagatctgcc gaaagattgg ctgctgat                               38

<210> SEQ ID NO 33
<211> LENGTH: 38
<212> TYPE: DNA
<213> ORGANISM: Artificial Sequence
<220> FEATURE:
<223> OTHER INFORMATION: primer

<400> SEQUENCE: 33
gtaccaattg tacagctgaa aatacatcgg cgcctact                               38

<210> SEQ ID NO 34
<211> LENGTH: 38
<212> TYPE: DNA
<213> ORGANISM: Artificial Sequence
<220> FEATURE:
<223> OTHER INFORMATION: primer

<400> SEQUENCE: 34
acctgacgtc tagatctggc cgctttcacc atttcctt                               38
```

<210> SEQ ID NO 35
<211> LENGTH: 39
<212> TYPE: DNA
<213> ORGANISM: Artificial Sequence
<220> FEATURE:
<223> OTHER INFORMATION: primer

<400> SEQUENCE: 35
gtaccaattg tacagctgcg atgaaaatct gcgcggtag                              39

<210> SEQ ID NO 36
<211> LENGTH: 38
<212> TYPE: DNA
<213> ORGANISM: Artificial Sequence
<220> FEATURE:
<223> OTHER INFORMATION: primer

<400> SEQUENCE: 36
cgtgttaacc ggtgagcttt ctaccgaaat accgccgt                               38

<210> SEQ ID NO 37
<211> LENGTH: 38
<212> TYPE: DNA
<213> ORGANISM: Artificial Sequence
<220> FEATURE:
<223> OTHER INFORMATION: primer

<400> SEQUENCE: 37
tggatcctct agtgagctaa ccacgccgaa aacctaac                               38

<210> SEQ ID NO 38
<211> LENGTH: 1224
<212> TYPE: DNA
<213> ORGANISM: Artificial Sequence
<220> FEATURE:
<223> OTHER INFORMATION: recombinant ALA synthase

<400> SEQUENCE: 38
atggactaca acttggcctt ggacaccgcc ttgaaccgct tgcacaccga aggccgctac        60
cgcaccttca tcgacatcga acgccgcaaa ggcgccttcc cgaaagccat gtggcgcaaa      120
ccggacggca gcgaaaaaga aatcaccgtc tggtgcggca cgactactt gggcatgggc       180 caacacccgg tcgtcttggg cgccatgcac gaagccttgg acagcaccgg cgccggcagc      240
ggcggcaccc gcaacatcag cggcaccacc ttgtaccaca aacgcttgga agccgaattg      300
gccgacttgc acggcaaaga agccgccttg gtcttcagca cgcctacat cgccaacgac       360 gccaccttga gcaccttgcc gcaattgatc ccgggcttgg tcatcgtcag cgacaaattg      420
aaccacgcca gcatgatcga aggcatccgc gcagcggca ccgaaaaaca catcttcaaa       480
cacaacgact ggacgacttt gccgcgcatc ttgaccagca tcggcaaaga ccgcccgatc      540
ttggtcgcct tcgaaagcgt ctacagcatg acggcgact tcggccgcat cgaagaaatc      600
tgcgacatcg ccgacgaatt cggcgccttg aaatacatcg acgaagtcca cgccgtcggc      660
atgtacggcc cgcgcggcgg cggcgtcgcc gaacgcgacg gcttgatgga ccgcatcgac      720
atcatcaacg gcaccttggg caaagcctac ggcgtcttcg gcggctacat cgccgccagc      780
agcaaaatgt gcgacgccgt ccgcagctac gccccgggct tcatcttcag caccagcttg      840
ccgccggtcg tcgccgccgg cgccgccgcc agcgtccgcc acttgaaagg cgacgtcgaa      900
ttgcgcgaaa acaccaaac ccaagcccgc atcttgaaaa tgcgcttgaa aggcttgggc      960
ttgccgatca tcgaccacgg cagccacatc gtcccggtcc acgtcggcga cccggtccac     1020

-continued

```
tgcaaaatga tcagcgacat gttgttggaa cacttcggca tctacgtcca accgatcaac    1080
ttcccgaccg tcccgcgcgg caccgaacgc ttgcgcttca ccccgagccc ggtccacgac    1140
agcggcatga tcgaccactt ggtcaaagcc atggacgtct tgtggcaaca ctgcgccttg    1200
aaccgcgccg aagtcgtcgc ctaa                                          1224
```

<210> SEQ ID NO 39
<211> LENGTH: 407
<212> TYPE: PRT
<213> ORGANISM: Artificial Sequence
<220> FEATURE:
<223> OTHER INFORMATION: recombinant ALA synthase

<400> SEQUENCE: 39

```
Met Asp Tyr Asn Leu Ala Leu Asp Thr Ala Leu Asn Arg Leu His Thr
1               5                   10                  15

Glu Gly Arg Tyr Arg Thr Phe Ile Asp Ile Glu Arg Arg Lys Gly Ala
            20                  25                  30

Phe Pro Lys Ala Met Trp Arg Lys Pro Asp Gly Ser Glu Lys Glu Ile
        35                  40                  45

Thr Val Trp Cys Gly Asn Asp Tyr Leu Gly Met Gly Gln His Pro Val
    50                  55                  60

Val Leu Gly Ala Met His Glu Ala Leu Asp Ser Thr Gly Ala Gly Ser
65                  70                  75                  80

Gly Gly Thr Arg Asn Ile Ser Gly Thr Thr Leu Tyr His Lys Arg Leu
                85                  90                  95

Glu Ala Glu Leu Ala Asp Leu His Gly Lys Glu Ala Ala Leu Val Phe
            100                 105                 110

Ser Ser Ala Tyr Ile Ala Asn Asp Ala Thr Leu Ser Thr Leu Pro Gln
        115                 120                 125

Leu Ile Pro Gly Leu Val Ile Val Ser Asp Lys Leu Asn His Ala Ser
    130                 135                 140

Met Ile Glu Gly Ile Arg Arg Ser Gly Thr Glu Lys His Ile Phe Lys
145                 150                 155                 160

His Asn Asp Leu Asp Asp Leu Arg Arg Ile Leu Thr Ser Ile Gly Lys
                165                 170                 175

Asp Arg Pro Ile Leu Val Ala Phe Glu Ser Val Tyr Ser Met Asp Gly
            180                 185                 190

Asp Phe Gly Arg Ile Glu Glu Ile Cys Asp Ile Ala Asp Glu Phe Gly
        195                 200                 205

Ala Leu Lys Tyr Ile Asp Glu Val His Ala Val Gly Met Tyr Gly Pro
    210                 215                 220

Arg Gly Gly Gly Val Ala Glu Arg Asp Gly Leu Met Asp Arg Ile Asp
225                 230                 235                 240

Ile Ile Asn Gly Thr Leu Gly Lys Ala Tyr Gly Val Phe Gly Gly Tyr
                245                 250                 255

Ile Ala Ala Ser Ser Lys Met Cys Asp Ala Val Arg Ser Tyr Ala Pro
            260                 265                 270

Gly Phe Ile Phe Ser Thr Ser Leu Pro Pro Val Ala Ala Gly Ala
        275                 280                 285

Ala Ala Ser Val Arg His Leu Lys Gly Asp Val Glu Leu Arg Glu Lys
    290                 295                 300

His Gln Thr Gln Ala Arg Ile Leu Lys Met Arg Leu Lys Gly Leu Gly
305                 310                 315                 320
```

-continued

```
Leu Pro Ile Ile Asp His Gly Ser His Ile Val Pro Val His Val Gly
            325                 330                 335

Asp Pro Val His Cys Lys Met Ile Ser Asp Met Leu Leu Glu His Phe
        340                 345                 350

Gly Ile Tyr Val Gln Pro Ile Asn Phe Pro Thr Val Pro Arg Gly Thr
            355                 360                 365

Glu Arg Leu Arg Phe Thr Pro Ser Pro Val His Asp Ser Gly Met Ile
370                 375                 380

Asp His Leu Val Lys Ala Met Asp Val Leu Trp Gln His Cys Ala Leu
385                 390                 395                 400

Asn Arg Ala Glu Val Val Ala
            405
```

<210> SEQ ID NO 40
<211> LENGTH: 21
<212> TYPE: DNA
<213> ORGANISM: Artificial Sequence
<220> FEATURE:
<223> OTHER INFORMATION: primer

<400> SEQUENCE: 40
caataaggat ccccaggcat c                                         21

<210> SEQ ID NO 41
<211> LENGTH: 23
<212> TYPE: DNA
<213> ORGANISM: Artificial Sequence
<220> FEATURE:
<223> OTHER INFORMATION: primer

<400> SEQUENCE: 41
ccatatgaga tctcctttaa cag                                       23

<210> SEQ ID NO 42
<211> LENGTH: 45
<212> TYPE: DNA
<213> ORGANISM: Artificial Sequence
<220> FEATURE:
<223> OTHER INFORMATION: primer

<400> SEQUENCE: 42
gttaaaggag atctcatatg gattaccggc gcttttcga gacgg                45

<210> SEQ ID NO 43
<211> LENGTH: 46
<212> TYPE: DNA
<213> ORGANISM: Artificial Sequence
<220> FEATURE:
<223> OTHER INFORMATION: primer

<400> SEQUENCE: 43
gatgcctggg gatccttatt gcgcggcgag cttgatctcg ggatag              46

<210> SEQ ID NO 44
<211> LENGTH: 56
<212> TYPE: DNA
<213> ORGANISM: Artificial Sequence
<220> FEATURE:
<223> OTHER INFORMATION: primer

<400> SEQUENCE: 44
cacatacact gttaaaggag atctcatatg gactacaact tggccttgga caccgc   56

```
<210> SEQ ID NO 45
<211> LENGTH: 53
<212> TYPE: DNA
<213> ORGANISM: Artificial Sequence
<220> FEATURE:
<223> OTHER INFORMATION: primer

<400> SEQUENCE: 45
cgttttattt gatgcctggg gatcctcagg cgacgacttc ggcgcggttc aag          53

<210> SEQ ID NO 46
<211> LENGTH: 517
<212> TYPE: DNA
<213> ORGANISM: Artificial Sequence
<220> FEATURE:
<223> OTHER INFORMATION: DNA fragment

<400> SEQUENCE: 46
catctcggcc gggtcggcaa tagcgcggac cactaaaaac ggcaactggg cattcgcggc    60
ggttcggccg accgccgcgc tttccatgtc gagggcgacg gcgccggtct gttcgaacaa   120
ttgccgcttt tcctcgcgtt gcccgacgat ccggccactt tccagtaaag tgccggagcc   180
gacggcttgg tggtccgcca gcaggttttgc caaacgttgc cgccaagacg gatcggtagc   240
caaactatgc cgatcctggg tgaggacgcg ttccggcaag accaaatccc ccggtcgccg    300
atcttgagcc aatgccgcgg cgcagcccca gctgattagc cgattcgcac cccggtcgat   360
taacccggcg gcggcttttt cggcgttggc cgggccggcg ccggagtaac tgagcagtac   420
gccgccaccg atggcatggc actcgcccag cgcaaatttg cgcttggtca gcgtgctaag   480
ctcttcgggt agggcgacga cgattccgca actcacg                            517

<210> SEQ ID NO 47
<211> LENGTH: 42
<212> TYPE: DNA
<213> ORGANISM: Artificial Sequence
<220> FEATURE:
<223> OTHER INFORMATION: primer

<400> SEQUENCE: 47
acgtctagat ctgaattcca tctcggccgg gtcggcaata gc                       42

<210> SEQ ID NO 48
<211> LENGTH: 38
<212> TYPE: DNA
<213> ORGANISM: Artificial Sequence
<220> FEATURE:
<223> OTHER INFORMATION: primer

<400> SEQUENCE: 48
atatgcatcc atggtacccg tgagttgcgg aatcgtcg                            38

<210> SEQ ID NO 49
<211> LENGTH: 515
<212> TYPE: DNA
<213> ORGANISM: Artificial Sequence
<220> FEATURE:
<223> OTHER INFORMATION: DNA fragment

<400> SEQUENCE: 49
ggcgattcct tatggtccag tgtgagatac gggtgaatac tgccagtcag gggttttttag    60 gccgctgctg gtgagattga aaagcagtga caacagccag ttgctgcgcg ccgataattt   120
gctggcgata atcgtggcct tgacgctgtt gcggctgatc ttgacctggt tggattcgtt   180
```

```
gaaatccaga tgctgtttga ttttttttcaa ggtcaacacc gccatgccca gtgcccacag    240
gcagaaattg cggatgccgg tttcatggct gggcagcaac tgggtgtagg tcagcgcgtt    300
ttgcaagtgg ccgtgagcga tgccgatcaa gcgttccagg cctttgcgga agcgttcgtc    360
gttggtggtc ggcgtcagat cggccaaatc gaagccggtt tcgtcgaaaa tatcttgcgg    420
cagccagcat acgccgcgtt tggcgtcgtc ccagatgtct ttcagaatgt tggtcatctg    480
caaaccctgg ccgaacgata ccgataactt caaca                               515
```

```
<210> SEQ ID NO 50
<211> LENGTH: 36
<212> TYPE: DNA
<213> ORGANISM: Artificial Sequence
<220> FEATURE:
<223> OTHER INFORMATION: primer

<400> SEQUENCE: 50
ggccctacgt acgcgtggcg attccttatg gtccag                               36

<210> SEQ ID NO 51
<211> LENGTH: 38
<212> TYPE: DNA
<213> ORGANISM: Artificial Sequence
<220> FEATURE:
<223> OTHER INFORMATION: primer

<400> SEQUENCE: 51
ctgtcctcta gtgagctctg ttgaagttat cggtatcg                             38

<210> SEQ ID NO 52
<211> LENGTH: 42
<212> TYPE: DNA
<213> ORGANISM: Artificial Sequence
<220> FEATURE:
<223> OTHER INFORMATION: primer

<400> SEQUENCE: 52
acgtctagat ctgaattcca tctcggccgg gtcggcaata gc                        42

<210> SEQ ID NO 53
<211> LENGTH: 38
<212> TYPE: DNA
<213> ORGANISM: Artificial Sequence
<220> FEATURE:
<223> OTHER INFORMATION: primer

<400> SEQUENCE: 53
ctgtcctcta gtgagctctg ttgaagttat cggtatcg                             38

<210> SEQ ID NO 54
<211> LENGTH: 1680
<212> TYPE: DNA
<213> ORGANISM: Artificial Sequence
<220> FEATURE:
<223> OTHER INFORMATION: recombinant budB

<400> SEQUENCE: 54
atggacaaac agtatccggt acgccagtgg gcgcacggcg ccgatctcgt cgtcagtcag     60
ctggaagcac agggggtacg ccaggtgttc ggcatccccg gcgccaaaat cgacaaggtc    120
ttcgattcac tgctggattc ctccattcgc attattccgg tacgccacga agccaacgcc    180
gcatttatgg ccgccgccgt cggacgtatt accggcaaag cgggcgtggc gctggtcacc    240
tccggtccgg gttgttctaa cctgatcacc ggcatggcca ccgcgaacag cgaaggcgac    300
```

```
ccggtggtgg ccctgggcgg cgcggtaaaa cgcgccgata aagccaaaca ggtccaccag      360
agtatggata cggtggcgat gttcagcccg gtcaccaaat acgccgtcga ggtgacggcg      420
ccggatgcgc tggcggaagt ggtctccaac gccttccgcg ccgccgagca gggccggccg      480
ggcagcgcgt tcgttagcct gccgcaggat gtggtcgatg ccccggtcag cggcaaagta      540
ctgccggcca gcggggcccc gcagatgggc gccgcgccgg atgatgccat cgaccaggtg      600
gcgaagctta tcgcccaggc gaagaacccg atcttcctgc tcggcctgat ggccagccag      660
ccggaaaaca gcaaggcgct cgccgtttg ctggagacca gccatattcc agtcaccagc      720
acctatcagg ccgccggagc ggtgaatcag gataacttct ctcgcttcgc cggccgggtt      780
gggctgttta acaaccaggc cggggaccgt ctgctgcagc ttgccgacct ggtgatctgc      840
atcggctaca gcccggtgga atacgaaccg gcgatgtgga acagcggcaa cgcgacgctg      900
gtgcacatcg acgtgctgcc cgcctatgaa gagcgcaact acaccccgga tgtcgagctg      960
gtaggcgata tcgccggcac tctcaacaag ctggcgcaaa atatcgatca tcggctggtg     1020
ctctccccgc aggcggcgga gatcctccgc gaccgccagc accagcgcga gctgctggac     1080
cgccgcggcg cgcagctcaa ccagtttgcc ctgcatccgc tgcgtatcgt tcgcgccatg     1140
caggacatcg tcaacagcga cgtcacgttg accgtggaca tgggcagctt ccatatctgg     1200
attgcccgct acctgtacag cttccgcgcc cgccaggtga tgatctccaa cggccagcag     1260
accatgggcg tcgccctgcc ctgggccatc ggcgcctggc tggtcaatcc tgagcgcaaa     1320
gtggtctccg tctccggcga cggcggcttc ctgcagtcga gcatggagct ggagaccgcc     1380
gtccgcctga agccaacgt gctgcacctg atctgggtcg ataacggcta acacatggtg     1440
gccattcagg aagagaaaaa ataccagcgc ctgtccggcg tcgagtttgg gccgatggat     1500
tttaaagcct atgccgaatc cttcggcgcg aaagggtttg ccgtggaaag cgccgaggcg     1560
ctggagccga ccctgcgcgc ggcgatggac gtcgacggcc cggcggtagt ggccatcccg     1620
gtggattatc gcgataaccc gctgctgatg ggccagctgc atctgagtca gattctgtaa     1680
```

<210> SEQ ID NO 55
<211> LENGTH: 780
<212> TYPE: DNA
<213> ORGANISM: Artificial Sequence
<220> FEATURE:
<223> OTHER INFORMATION: recombinant budA

<400> SEQUENCE: 55

```
atgaatcatt ctgctgaatg cacctgcgaa gagagtctat gcgaaaccct gcgggcgttt       60
tccgcgcagc atcccgagag cgtgctctat cagacatcgc tcatgagcgc cctgctgagc      120 gggtttacg aaggcagcac caccatcgcc gacctgctga acacggcga tttcggcctc       180 ggcaccttta tgagctgga cggggagctg atcgccttca gcagtcaggt ctatcagctg       240
cgcgccgacg gcagcgcgcg caaagcccag ccggagcaga aaacgccgtt cgcggtgatg      300
acctggttcc agccgcagta ccggaaaacc tttgaccatc cggtgagccg ccagcagctg      360
cacgaggtga tcgaccagca aatcccctct gacaacctgt tctgcgccct gcgcatcgac      420
ggccatttcc gccatgccca tacccgcacc gtgccgcgcc agacgccgcc gtaccgggcg      480
atgaccgacg tactcgacga tcagccggtg ttccgcttta accagcgcga aggggtgctg      540 gtcgcttcc ggaccccgca gcatatgcag gggatcaacg tcgccgggta tcacgagcat      600
tttattaccg atgaccgcaa aggcggcggt cacctgctgg attaccagct cgaccacggg      660
```

```
gtgctgacct tcggcgaaat tcacaagctg atgatcgacc tgcccgccga cagcgcgttc    720
ctgcaggcta atctgcatcc cgataatctc gatgccgcca tccgttccgt agaaagttaa    780
```

<210> SEQ ID NO 56
<211> LENGTH: 771
<212> TYPE: DNA
<213> ORGANISM: Artificial Sequence
<220> FEATURE:
<223> OTHER INFORMATION: recombinant budC

<400> SEQUENCE: 56

```
atgaaaaaag tcgcacttgt taccggcgcc ggccagggga ttggtaaagc tatcgccctt     60
cgtctggtga aggatggatt tgccgtggcc attgccgatt ataacgacgc caccgccaaa    120
gcggtcgcct ccgaaatcaa ccaggccggc ggccgcgcca tggcggtgaa agtggatgtt    180
tctgaccgcg accaggtatt tgccgccgtc gaacaggcgc gcaaaacgct gggcggcttc    240
gacgtcatcg tcaacaacgc cggcgtggcc catccacgc cgatcgagtc cattaccccg     300
gagattgtcg acaaagtcta caacatcaac gtcaaagggg tgatctgggg catccaggca    360
gcggtcgagg cctttaagaa agagggtcac ggcgggaaaa tcatcaacgc tgttcccag    420 gccgccacg tcggcaaccc ggagctggcg gtatatagct cgagtaaatt cgcggtacgc    480
ggcttaaccc agaccgccgc tcgcgacctc gcgccgctgg gcatcacggt caacggctac    540
tgcccgggga ttgtcaaaac gccgatgtgg gccgaaattg accgccaggt gtccgaagcc    600
gccggtaaac cgctgggcta cggtaccgcc gagttcgcca aacgcatcac cctcggccgc    660
ctgtccgagc cggaagatgt cgccgcctgc gtctcctatc ttgccagccc ggattctgat    720
tatatgaccg gtcagtcatt gctgatcgac ggcggcatgg tgtttaacta a             771
```

<210> SEQ ID NO 57
<211> LENGTH: 3263
<212> TYPE: DNA
<213> ORGANISM: Artificial Sequence
<220> FEATURE:
<223> OTHER INFORMATION: recombinant budABC gene cluster

<400> SEQUENCE: 57

```
atgaatcatt ctgctgaatg cacctgcgaa gagagtctat gcgaaaccct gcgggcgttt     60
tccgcgcagc atcccgagag cgtgctctat cagacatcgc tcatgagcgc cctgctgagc    120 gggggtttacg aaggcagcac caccatcgcc gacctgctga acacggcga tttcggcctc    180 ggcacctttta tgagctgga cggggagctg atcgccttca gcagtcaggt ctatcagctg    240
cgcgccgacg gcagcgcgcg caaagcccag ccggagcaga aaacgccgtt cgcggtgatg    300
acctggttcc agccgcagta ccggaaaacc tttgaccatc cggtgagccg ccagcagctg    360
cacgaggtga tcgaccagca aatcccctct gacaacctgt tctgcgcccct gcgcatcgac    420 ggccattcc gccatgccca tacccgcacc gtgccgcgcc agacgccgcc gtaccgggcg    480
atgaccgacg tactcgacga tcagccggtg ttccgcttta accagcgcga aggggtgctg    540
gtcggcttcc ggaccccgca gcatatgcag gggatcaacg tcgccgggta tcacgagcat    600
tttattaccg atgaccgcaa aggcggcggt cacctgctgg attaccagct cgaccacggg    660
gtgctgacct tcggcgaaat tcacaagctg atgatcgacc tgcccgccga cagcgcgttc    720
ctgcaggcta atctgcatcc cgataatctc gatgccgcca tccgttccgt agaaagttaa    780
gggggtcaca tggacaaaca gtatccggta cgccagtggg cgcacggcgc cgatctcgtc    840
gtcagtcagc tggaagcaca ggggtacgcg caggtgttcg gcatccccgg cgccaaaatc    900
```

```
gacaaggtct tcgattcact gctggattcc tccattcgca ttattccggt acgccacgaa    960
gccaacgccg catttatggc cgccgccgtc ggacgtatta ccggcaaagc gggcgtggcg   1020
ctggtcacct ccggtccggg ttgttctaac ctgatcaccg gcatggccac cgcgaacagc   1080
gaaggcgacc cggtggtggc cctgggcggc gcggtaaaac gcgccgataa agccaaacag   1140
gtccaccaga gtatggatac ggtggcgatg ttcagcccgg tcaccaaata cgccgtcgag   1200
gtgacggcgc cggatgcgct ggcggaagtg gtctccaacg ccttccgcgc cgccgagcag   1260
ggccggccgg gcagcgcgtt cgttagcctg ccgcaggatg tggtcgatgg cccggtcagc   1320
ggcaaagtac tgccggccag cggggccccg cagatgggcg ccgcgccgga tgatgccatc   1380
gaccaggtgg cgaagcttat cgcccaggcg aagaacccga tcttcctgct cggcctgatg   1440
gccagccagc cggaaaacag caaggcgctg cgccgtttgc tggagaccag ccatattcca   1500
gtcaccagca cctatcaggc cgccggagcg gtgaatcagg ataacttctc tcgcttcgcc   1560
ggccgggttg ggctgtttaa caaccaggcc ggggaccgtc tgctgcagct tgccgacctg   1620
gtgatctgca tcggctacag cccggtggaa tacgaaccgg cgatgtggaa cagcggcaac   1680
gcgacgctgt tgcacatcga cgtgctgccc gcctatgaag agcgcaacta cacccccggat  1740
gtcgagctgg taggcgatat cgccggcact ctcaacaagc tggcgcaaaa tatcgatcat   1800
cggctggtgc tctccccgca ggcggcggag atcctccgcg accgcagca ccagcgcgag    1860
ctgctggacc gccgcggcgc gcagctcaac cagtttgccc tgcatccgct gcgtatcgtt   1920
cgcgccatgc aggacatcgt caacagcgac gtcacgttga ccgtggacat gggcagcttc   1980
catatctgga ttgcccgcta cctgtacagc ttccgcgccc gccaggtgat gatctccaac   2040
ggccagcaga ccatgggcgt cgccctgccc tgggccatcg gcgcctggct ggtcaatcct   2100
gagcgcaaag tggtctccgt ctccggcgac ggcggcttcc tgcagtcgag catggagctg   2160
gagaccgccg tccgcctgaa agccaacgtg ctgcacctga tctgggtcga taacggctac   2220
aacatggtgg ccattcagga agagaaaaaa taccagcgcc tgtccggcgt cgagtttggg   2280
ccgatggatt ttaaagccta tgccgaatcc ttcggcgcga aagggtttgc cgtggaaagc   2340
gccgaggcgc tggagccgac cctgcgcgcg gcgatggacg tcgacggccc ggcggtagtg   2400
gccatcccgg tggattatcg cgataacccg ctgctgatgg gccagctgca tctgagtcag   2460
attctgtaag tcatcacaat aaggaaagaa aaatgaaaaa agtcgcactt gttaccggcg   2520
ccggccaggg gattggtaaa gctatcgccc ttcgtctggt gaaggatgga tttgccgtgg   2580
ccattgccga ttataacgac gccaccgcca agcggtcgc ctccgaaatc aaccaggccg    2640
gcggccgcgc catggcggtg aaagtggatg tttctgaccg cgaccaggta tttgccgccg   2700
tcgaacaggc gcgcaaaacg ctgggcgcct cgacgtcat cgtcaacaac gccggcgtgg    2760
cgccatccac gccgatcgag tccattaccc cggagattgt cgacaaagtc tacaacatca   2820
acgtcaaagg ggtgatctgg ggcatccagg cagcggtcga ggcctttaag aaagagggtc   2880
acggcgggaa aatcatcaac gcctgttccc aggccggcca cgtcggcaac ccggagctgg   2940
cggtatatag ctcgagtaaa ttcgcggtac gcggcttaac ccagaccgcc gctcgcgacc   3000
tcgcgccgct gggcatcacg gtcaacggct actgccgggg gattgtcaaa cgccgatgt    3060
gggccgaaat tgaccgccag gtgtccgaag ccgccggtaa accgctgggc tacggtaccg   3120
ccgagttcgc caaacgcatc accctcggcc gcctgtccga gcggaagat gtcgccgcct    3180
gcgtctccta tcttgccagc ccggattctg attatatgac cggtcagtca ttgctgatcg   3240
```

```
acggcggcat ggtgtttaac taa                                              3263
```

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58

```
tagttgtcgg gaagatgcgt                                                    20
```

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59

```
agctgtttcc tgtgtgaata                                                    20
```

<210> SEQ ID NO 60
<211> LENGTH: 42
<212> TYPE: DNA
<213> ORGANISM: Artificial Sequence
<220> FEATURE:
<223> OTHER INFORMATION: primer

<400> SEQUENCE: 60

```
ttcacacagg aaacagctat gaatcattct gctgaatgca cc                            42
```

<210> SEQ ID NO 61
<211> LENGTH: 39
<212> TYPE: DNA
<213> ORGANISM: Artificial Sequence
<220> FEATURE:
<223> OTHER INFORMATION: primer

<400> SEQUENCE: 61

```
gcatcttccc gacaactatt agttaaacac catgccgcc                                39
```

<210> SEQ ID NO 62
<211> LENGTH: 1164
<212> TYPE: DNA
<213> ORGANISM: Artificial Sequence
<220> FEATURE:
<223> OTHER INFORMATION: recombinant methanol dehydrogenase

<400> SEQUENCE: 62

```
atggaaatga cgaacactca gtcagccttc tttatgccta cgtaaatttt gttcggcgcg         60
ggtagcgtga atgaggtcgg tacccgcttg gcagatttag gtgtgaaaaa agcgctgctg        120
gttaccgatg cgggtctgca cggcttggga ctgtcggaaa aaattagtag cattatccgt        180
gccgccgggg tcgaagtgtc gatttttcct aaagcggagc cgaatcctac agataagaat        240
gtggccgaag gcttggaagc gtacaacgcg gaaaactgcg atagcattgt gactttgggc        300
ggcggtagca gccatgatgc cggcaaagca atcgcgttgg tggcagcgaa cggcggcaaa        360
attcacgact atgaaggcgt cgatgtgagt aaagaaccta tggtcccact tattgccatt        420
aataccaccg caggtacggg tagcgagctg accaagttca ctattatcac tgacaccgaa        480
cgtaaagtga agatggcaat cgtggataag catgtgactc cgaccctgag tattaatgac        540
ccagagttga tggtaggtat gccgcctagc ctgaccgcgg cgactgggct tgatgcgttg        600
```

| | |
|---|---|
| actcatgcga tcgaagcata tgtctcaacc ggtgccaccc cgatcaccga tgcgcttgcg | 660 |
| attcaagcga tcaaaatcat cagcaaatat ctgccgcgcg cggtggccaa tggcaaagat | 720 |
| attgaagccc gtgaacaaat ggcgtttgca cagagcttag cgggtatggc ctttaataac | 780 |
| gcgggattag gctatgtgca tgccatcgca catcaactgg gcggctttta taactttcct | 840 |
| catggcgttt gtaatgccgt gctgttacct tacgtttgtc gttttaattt aattagcaaa | 900 |
| gtggaacgct acgccgaaat cgcggcgttc ttaggcgaaa atgtggatgg cctgagcacg | 960 |
| tatgacgcgg cggaaaaagc gattaaagcc attgaacgca tggcgaaaga cctgaacatt | 1020 |
| cctaaaggtt ttaaggagtt aggcgcgaaa gaagaggata tcgaaaccct ggcaaagaat | 1080 |
| gcgatgaaag acgcgtgcgc gttgactaac cctcgcaagc cgaagctgga ggaggtcatt | 1140 |
| caaatcatta aaaatgcgat gtaa | 1164 |

<210> SEQ ID NO 63
<211> LENGTH: 1725
<212> TYPE: DNA
<213> ORGANISM: Artificial Sequence
<220> FEATURE:
<223> OTHER INFORMATION: recombinant formolase

<400> SEQUENCE: 63

| | |
|---|---|
| atggctatga ttactggtgg tgaactggtt gttcgtaccc tgattaaagc tggcgtagaa | 60 |
| catctgtttg gcctgcatgg cattcatatt gacaccattt ttcaggcttg cctggaccac | 120 |
| gacgtcccaa tcattgatac tcgccacgaa gcggcggcag ccacgctgc ggaaggttat | 180 |
| gcccgcgcgg gcgctaaact gggtgttgcc ctggtgaccg ctggcggtgg ctttaccaat | 240 |
| gccgttacgc cgatcgcgaa cgctcggacc gatcgcactc cggttctgtt cctgaccggt | 300 |
| tctggtgctc ttcgtgatga cgaaaccaac accctgcagg ccggtattga tcaggtggcc | 360 |
| atggcggccc cgatcacgaa atgggctcat cgtgttatgg caactgaaca catcccgcgt | 420 |
| ctggttatgc aggccattcg tgccgctctg agcgccccac gtggcccggt gctgctggat | 480 |
| ctgccatggg acatcctgat gaaccaaatc gatgaagatt ccgttatcat cccagacctg | 540 |
| gtgctgtctg ctcacggtgc ccatccagac ccggctgacc tggaccaggc tctggcactg | 600 |
| ctgcgtaaag ccgaacgccc agttatcgta ctgggctccg aggcgtcccg caccgcacgc | 660 |
| aagaccgcac tgagcgcatt cgtagcgcg accggtgtac cggttttcgc tgactatgaa | 720 |
| ggcctgtcca tgctgagcgg cctgccggac gctatgcgtg cggcctggt gcagaacctg | 780 |
| tactcctttg caaaagctga tgcagctccg gacctggtac tgatgctggg tgctcgtttc | 840 |
| ggtctgaaca ccggtcatgg ttccggtcaa ctgatcccgc attctgctca ggtgatccag | 900 |
| gtggatccag acgcgtgtga actgggtcgc ctgcaaggca tcgcgctggg tatcgtggct | 960 |
| gatgtaggtg gcaccattga agcgctggct caggcgaccg cacaggacgc cgcgtggccg | 1020 |
| gaccgcggcg actggtgcgc caaggtaact gacctggccc aggagcgtta cgcttccatc | 1080 |
| gcggctaaat ccagctctga acatgcgctg cacccgttcc acgcttctca ggttatcgcg | 1140 |
| aaacacgtgg acgcaggcgt gaccgtcgtt gcggatggtg gcctgactta tctgtggctg | 1200 |
| tccgaagtta tgtctcgtgt caaaccaggc ggcttcctgt gccacggcta tctgaacagc | 1260 |
| atgggtgtag gcttcggtac tgccctgggt gcgcaggttg cggatctgga ggcaggtcgt | 1320 |
| cgtaccatcc tggtgaccgg cgacggctct gttggttatt ccattggcga attcgacacc | 1380 |
| ctggtacgca acagctgcc gctgattgta attatcatga caaccagtc ttggggctgg | 1440 |

```
accctgcact ttcagcagct ggccgttggt cctaaccgtg tcaccggcac ccgcctggaa    1500
aatggttcct atcacggcgt tgctgcggca ttcggtgctg atggttacca cgtcgactct    1560
gtcgagagct tcagcgccgc tctggctcag gcactggcac acaaccgccc ggcatgcatc    1620
aacgttgctg tggccctgga cccgatcccg ccggaggaac tgatcctgat tggcatggac    1680
ccgtttgcgg gctccacgga gaatctgtat ttccaatccg gcgcg                    1725
```